United States Patent
Izsvák et al.

(10) Patent No.: US 11,814,643 B2
(45) Date of Patent: *Nov. 14, 2023

(54) ENHANCED SLEEPING BEAUTY TRANSPOSONS, KITS AND METHODS OF TRANSPOSITION

(71) Applicant: Max-Delbrück-Centrum für Molekulare Medizin in der Helmholtz-Gemeinschaft, Berlin-Buch (DE)

(72) Inventors: Zsuzsanna Izsvák, Berlin (DE); Zoltán Ivics, Berlin (DE); Christopher Kaufman, Pittsford, NY (US); Suneel Narayanavari, Würzburg (DE)

(73) Assignee: Max-Delbrück-Centrum für Molekulage Medizin in der Helmholtz-Gemeinschaft., Berlin-Buch (DE)

( * ) Notice: Subject to any disclaimer, the term of this patent is extended or adjusted under 35 U.S.C. 154(b) by 892 days.

This patent is subject to a terminal disclaimer.

(21) Appl. No.: 16/085,012

(22) PCT Filed: Mar. 15, 2017

(86) PCT No.: PCT/EP2017/056133
§ 371 (c)(1),
(2) Date: Sep. 14, 2018

(87) PCT Pub. No.: WO2017/158029
PCT Pub. Date: Sep. 21, 2017

(65) Prior Publication Data
US 2019/0169638 A1    Jun. 6, 2019

(30) Foreign Application Priority Data
Mar. 15, 2016 (EP) .................................... 16160499

(51) Int. Cl.
*C12N 15/90* (2006.01)
(52) U.S. Cl.
CPC .......... *C12N 15/90* (2013.01); *C12N 2800/90* (2013.01)
(58) Field of Classification Search
CPC ............................. C12N 15/90; C12N 2800/90
See application file for complete search history.

(56) References Cited

U.S. PATENT DOCUMENTS 8,227,432 B2 * 7/2012 Hackett .................... C12N 9/22
514/44 R
10,975,136 B2 * 4/2021 Uckert ................ C12N 9/1241

FOREIGN PATENT DOCUMENTS

| WO | 98/40510 A1 | 9/1998 |
| WO | 03/089618 | 10/2003 |
| WO | 2008106986 A1 | 9/2008 |

OTHER PUBLICATIONS

Pryputniewicz-Drobihska, D. "Regulated Complex Assembly Protects Cells From Aberrant Sleeping Beauty Transposition Events", Dissertation dated Mar. 8, 2010.
Field, A. et al. "Comparison of Lentiviral and Sleeping Beauty Mediated aβT Cell Receptor Gene Transfer", Plos One, Jun. 2013, vol. 8, Issue 6.
Walisko, O. et al. "Sleeping Beauty Transposanse Modulates Cell-Cycle Progression Through Interaction With MIZ-1", PNAS, Mar. 14, 2006, vol. 103, No. 11.
International Search Report and Written Opinion dated Jul. 3, 2017, from International Application No. PCT/EP2017/056133, 15 pages.
(Continued)

*Primary Examiner* — Nancy J Leith
(74) *Attorney, Agent, or Firm* — Meunier Carlin & Curfman LLC

(57) ABSTRACT

The present invention relates to enhanced Sleeping Beauty-type transposons and methods of transposition. In particular the invention relates to a polynucleotide comprising a cargo nucleic acid flanked by a left and a right inverted repeat/direct repeat (IR/DR), wherein IR/DRs, having specific sequences, are recognized by a Sleeping Beauty transposase protein and the polynucleotide is capable of integrating into the DNA of a cell. The invention also relates to a kit for transposing a nucleic acid comprising said polynucleotide as well as to further components such as co-factors of transposition capable of depleting a component of the FACT (facilitates chromatin transcription) complex, namely, SSRP1 and/or SUPT16H/SPT16, or an inhibitor of cathepsin selected from the group comprising H, S, V, and L; or a cofactor capable of depleting or inhibiting HSP90; or a factor temporally arresting cells cell cycle in cell cycle phase G0/G1, G1/S, or G2/M; or a factor inhibiting the ubiquitination of PCNA, or cells wherein these components have been knocked down or inhibited, or the cell cyle arrested in any of said stages. Alternatively or additionally, the kit may comprise as a co-factor of transposition an agent capable of increasing concentration and/or signaling of ATR or a cell wherein concentrationand/or signaling of ATR are increased. The invention further provides methods using said transposon polynucleotide as well as host cells and pharmaceutical compositions. It also relates to use of said co-factors of transposition or specific cells for enhancing transposition efficiencies, e.g., for preparing genetically modified nucleic acids or cells.

23 Claims, 13 Drawing Sheets

Figure 1:
Figure 1:
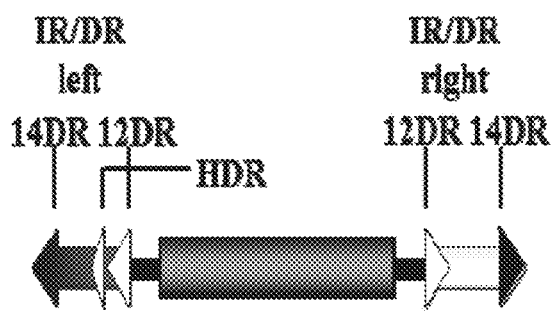

Specification includes a Sequence Listing.

(56) References Cited

OTHER PUBLICATIONS

Boehme, et al., 2016. A High-Capacity Adenoviral Hybrid Vector System Utilizing the Hyperactive Sleeping Beauty Transposase SB100X for Enhanced Integration. Mol Ther Nucleic Acids 5, e337.
Carpentier CE, et al., 2014. NMR structural analysis of Sleeping Beauty transposase binding to DNAProt Sci. 23:23-33.
Cliby et al., 1998. Overexpression of a kinase-inactive ATR protein causes sensitivity to DNA-damaging agents and defects in cell cycle checkpointsEMBO J. 17(1):159-69.
Cui et al., 2002. Structure-function analysis of the inverted terminal repeats of the Sleeping Beauty transposon. J. Mol. Biol. 318 (5): 1221-1235.
Czerny T, et al., 1993. DNA sequence recognition by Pax proteins: bipartite structure of the paired domain and its binding site. Genes Dev., 7: 2048-61.
Dawson A and Finnegan DJ, 2003. Excision of the Drosophila Mariner Transposon Mos1: Comparison with Bacterial Transposition and V(D)J Recombination. Mol Cell. 11: 225-35.
Franz G and Savakis C, 1991. Minos, a new transposable element from *Drosophila hydei*, is a member of the Tc1-like family of transposons. Nucleic Acids Res, 19: 6646.
Goryshin et al., 1998. Tn5 in Vitro Transposition. JBC 273, 7367-7374.
Hesse, JE et al., 1989. V(D)J recombination: a functional definition of the joining signals. Genes Development, 3:1053-61.
Hickman AB, et al., 2014. Structural Basis of hAT Transposon End Recognition by Hermes, an Octameric DNA Transposase from Musca domesticaCell, 158: 353-67.
Huang et al., 2006. Modulation of nucleosome-binding activity of FACT by poly(ADP-ribosyl)ationNucleic Acids Res. 34:2398-2407.
Ivics et al., 1997, Molecular Reconstruction of Sleeping Beauty, a Tc1-like Transposon from Fish, and Its Transposition n Human Cells. Cell 91:501-510.
Izsvak Z, et al., 2002. Involvement of a Bifunctional, Paired-like DNA-binding Domain and a Transpositional Enhancer in Sleeping Beauty Transposition. J Biol Chem, 277: 34581-8.
Izsvak Z, et al., 1995. Characterization of a Tc1-like transposable element in zebrafish (*Danio rerio*). Mol Gen Genet. 247: 312-22.
Izsvak Z, et al., 2000. Sleeping Beauty, a Wide Host-range Transposon Vector for Genetic Transformation in Vertebrates. J Mol Biol, 302: 93-102.
Izsvak Z, et al., 2004. Healing the Wounds Inflicted by Sleeping Beauty Transposition by Double-Strand Break Repair in Mammalian Somatic Cells. Mol Cell, 13:279-90.
Kay et al., 2010. A robust system for production of minicircle DNANA vectors. Nature Biotechnology 28, 1287-1289.
Kumari et al., 2009. A Role for SSRP1 in Recombination-Mediated DNA Damage Response. J Cell Biochem. 108:508-518.
Lupardus et al., 2002. A requirement for replication in activation of the ATR-dependent DNA damage checkpoint. Genes Dev 16(18):2327-32.

Marie et al, 2010. pFARs, Plasmids free of antibiotic resistance markers, display high-level transgene expression in muscle, skin and tumour cells. J Gen Med 12(4), 323-332.
Mátés L1, et al. Molecular evolution of a novel hyperactive Sleeping Beauty transposase enables robust stable gene transfer in vertebrates. Nat Genet. Jun. 2009;41(6):753-61).
Miskey C, et al., 2003. The Frog Prince: a reconstructed transposon from Rana pipiens with high transpositional activity in vertebrate cells. Nucleic Acids Res, 31: 6873-81.
Mizuuchi K, et al., 1992. Polynucleotidyl Transfer Reactions in Transpositional DNA Recombination. J Biol Chem., 267:21273-6.
Narayanavari et al., 2017. Sleeping Beauty transposition: from biology to applications. Crit Rev Biochem Mol Biol. 52(1):18-44.
Orphanides et al., 1999. The chromatin-specific transcription elongation factor FACT comprises human SPT16 and SSRP1 proteins Nature 400:284-288.
Plasterk RH, et al., 1999. Resident aliens the Tc1/mariner superfamily of transposable elements. Trends Genet, 15:326-32.
Richter et al., 2016. In vivo transduction of primitive mobilized hematopoietic stem cells after intravenous injection of integrating adenovirus vectors. Blood 128(18):2206-2217.
Richardson JM, et al., 2006. Mechanism of Mos1 transposition: insights from structural analysis. Embo J., 25: 1324-34.
Richardson JM, et al., 2009. Molecular Architecture of the Mos1 Paired-End Complex: The Structural Basis of DNA Transposition in a Eukaryote. Cell, 138:1096-108.
Rosenzweig B, et al., 1983. Sequence of the C. elegans transposable element Tc1. Nucleic Acids Res, 11: 4201-9.
Sarkaria et al., 1999, Inhibition of ATM and ATR Kinase Activities by the Radiosensitizing Agent, Caffeine. Cancer Res. 59(17):4375-82.
Solinger et al., 2002, Rad54, a Swi2/Snf2-like Recombinational Repair Protein, Disassembles Rad51:dsDNA Filaments. Mol Cell. 10:1175-1188.
Tosi LR and Beverley SM, 2000. cis and trans factors affecting Mos1 mariner evolution and transposition in vitro, and ts potential for functional genomics. Nucleic Acids Res., 28: 784-90.
VanDenmark et al., 2006, The Structure of the yFACT Pob3-M Domain, Its Interaction with the DNA Replication Factor RPA, and a Potential Role in Nucleosome Deposition. Mol Cell. 22:363-374.
Wright et al., 1991. Cyclic Amplification and Selection of Targets (CASTing) for the Myogenin Consensus Binding Site. Mol Cell Biol. 11:4104-10.
Yant SR, et al. Mutational analysis of the N-terminal DNA-binding domain of sleeping beauty transposase: critical residues for DNA binding and hyperactivity in mammalian cells. Mol Cell Biol. Oct. 2004;24(20):9239-47.
Yant et al., 2002. Transposition from a gutless adeno-transposon vector stabilizes transgene expression in vivo. Nat Biotechnol 20, 999-1005.
Zhang et al, 2013. Integration Profile and Safety of an Adenovirus Hybrid-Vector Utilizing Hyperactive Sleeping Beauty Transposase for Somatic Integration. PLoS One 8(10):e75344.
Siegal, Mark L., and Joanna Masel. "Hsp90 depletion goes wild." BMC biology 10.1 (2012): 1-3.
Formosa, "The role of FACT in making and breaking nucleosomes," Biochimica et Biophysica Acta 1819 (2021), pp. 247-255.

* cited by examiner

A

*Mariner*

B

*Sleeping Beauty*

SB left outer 14 DR (SEQ ID NO: 32

SB right outer 12 DR (SEQ ID NO: 33)

A
(i)

(ii)

ENHANCED SLEEPING BEAUTY TRANSPOSONS, KITS AND METHODS OF TRANSPOSITION

SEQUENCE LISTING

A Sequence Listing was filed in electronic format on Mar. 7, 2023. The Sequence Listing was provided as a file entitled "10933_008US1_ST25.txt", created Apr. 1, 2022, which is 18,892 bytes in size. The information in the electronic format of the Sequence Listing is incorporated herein by reference in its entirety.

The present invention relates to enhanced Sleeping Beauty-type transposons and methods of transposition. In particular, the invention relates to a polynucleotide comprising a cargo nucleic acid flanked by a left and a right inverted repeat/direct repeat (IR/DR), wherein IR/DRs, having specific sequences, are recognized by a Sleeping Beauty transposase protein and the polynucleotide is capable of integrating into the DNA of a cell. The invention also relates to a kit for transposing a nucleic acid comprising said polynucleotide as well as to further components such as co-factors of transposition capable of depleting a component of the FACT (facilitates chromatin transcription) complex, namely, SSRP1 and/or SUPT16H/SPT16, or an inhibitor of cathepsin selected from the group comprising H, S, V, and L; or a cofactor capable of depleting or inhibiting HSP90; or a factor temporally arresting cells cell cycle in cell cycle phase G0/G1, G1/S, or G2/M; or a factor inhibiting the ubiquitination of PCNA, or cells wherein these components have been knocked down or inhibited, or the cell cyle arrested in any of said stages. Alternatively or additionally, the kit may comprise as a co-factor of transposition an agent capable of increasing concentration and/or signaling of ATR or a cell wherein concentration and/or signaling of ATR are increased. The invention further provides methods using said transposon polynucleotide as well as host cells and pharmaceutical compositions. It also relates to use of said co-factors of transposition or specific cells for enhancing transposition efficiencies, e.g., for preparing genetically modified nucleic acids or cells.

DNA recombination inherently involves breakage and joining of distant DNA sites. The best studied recombination mechanisms in eukaryotes include V(D)J recombination (a transposition-like process that generates the immunglobulin repertoire of the adaptive immune system in vertebrates) and transposition of the mariner and Sleeping Beauty transposable elements. These recombination reactions require two major functional components: a recombinase protein and specific DNA sites at which the recombinase binds and executes recombination. A highly conserved catalytic domain, containing a DDE signature (D=aspartic acid, E=glutamic acid), commonly characterizes many recombinases. This DDE superfamily is widespread from prokaryotes to humans, including the bacterial IS elements, the Tc1/mariner family of DNA-transposons, human immunodeficiency virus integrase or the RAG1 recombinase of V(D)J recombination. Our understanding of transpositional mechanisms in eukaryotes gradually improves due to growing numbers of solved crystal structures of various recombinases. Still, despite of the shared chemical reactions performed by the catalytic domain, there are important differences how the different elements process the reaction. While all DDE recombinases initiate the recombination reaction with a single-stranded nick at the end of the transposon (Mizuuchi K, et al., 1992. J Biol Chem., 267: 21273-6; Hickman A B, et al., 2014. Cell, 158: 353-67), the second strand processing can vary. Cleavage of the second strand is often achieved via a hairpin intermediate, but not in the mariner elements and Sleeping Beauty (Dawson A and Finnegan D J, 2003. Mol Cell. 11: 225-35; Izsvak Z, et al., 2004. Mol Cell, 13: 279-90), where the double-strand cleavage is the result of two sequential hydrolysis reactions by the recombinase (Richardson J M, et al., 2006. Embo J., 25: 1324-34; Richardson J M, et al., 2009. Cell, 138: 1096-108.).

Members of the Tc1/mariner superfamily, including the Sleeping Beauty (SB) transposon, are intensively studied eukaryotic elements. SB became an indispensable genetic tool to manipulate vertebrate genomes. Both mariner and SB transpositions are sensitive to the size of the transposon and large elements transpose with lower frequencies compared to wild type. Despite such similarities, mariner and SB transposition seem to have significant differences. The regulation, including the strategy to enforce a synapsis of the transposon ends, as well as the requirement for such a synapsis, also varies among recombinases. While mariners have short TIRs with one transposon binding site at each transposon end (Rosenzweig B, et al., 1983. Nucleic Acids Res, 11: 4201-9; Tosi L R and Beverley S M, 2000. Nucleic Acids Res., 28: 784-90.), Sleeping Beauty (SB) belongs to the indirect repeat/direct repeat (IR/DR) subfamily of transposons, possessing two transposase binding sites (represented by direct repeats) at each transposon ends (Franz G and Savakis C, 1991. Nucleic Acids Res, 19: 6646; Izsvak Z, et al., 1995. Mol Gen Genet. 247: 312-22; Ivics Z, et al., 1997. Cell, 91: 501-10; Miskey C, et al., 2003. Nucleic Acids Res, 31: 6873-81; Plasterk R H, et al., 1999. Trends Genet, 15: 326-32) (FIG. 1A). The left IR contains an additional a half-direct repeat (HDR) motif that acts as an enhancer in SB transposition (Izsvak Z, et al., 2002. J Biol Chem, 277: 34581-8.) Despite the observation that the IR/DR is an absolute requirement of SB transposition (Izsvak Z, et al., 2000. J Mol Biol, 302: 93-102.), our understanding of its role in the transposition process is enigmatic.

Different variants of SB transposons are known in the art 8,227,432, Cui et al., 2002. Structure-function analysis of the inverted terminal repeats of the *Sleeping Beauty transposon*". J. Mol. Biol. 318 (5): 1221-1235; Izsvák et al. 2000. *Sleeping Beauty*, a wide host-range transposon vector for genetic transformation in vertebrates. J. Mol. Biol. 302 (1): 93-102). Commercially available plasmids containing Sleeping Beauty transposons are designated pT, pT2 or pT3 (Yant S R, et al. Mutational analysis of the N-terminal DNA-binding domain of sleeping beauty transposase: critical residues for DNA binding and hyperactivity in mammalian cells. Mol Cell Biol. 2004 October; 24(20):9239-47.).

Still, there is a need in the art for transposons having an enhanced efficiency, and enhanced transposon systems, kits and methods. This problem was addressed by the present inventors. The invention is described in the appended claims and the description.

In particular, the invention provides a polynucleotide comprising a transposon comprising a cargo nucleic acid flanked by a left and a right inverted repeat/direct repeat (IR/DR), wherein
  (i) the transposon is capable of being mobilized by a Sleeping Beauty transposase protein;
  (ii) the left IR/DR comprises an outer left DR motif and an inner left DR motif, wherein the outer left DR motif comprises the nucleotide sequence of SEQ ID NO:1 and the inner left DR motif comprises the nucleotide sequence of SEQ ID NO: 2; and
  (iii) the right IR/DR comprises an outer right DR motif and an inner right DR motif, wherein the outer right DR motif comprises a reverse complement of the nucleotide sequence of SEQ ID NO:1 and the inner right DR motif comprises a reverse complement of the nucleotide sequence of SEQ ID NO: 2.

The invention also provides the complimentary polynucleotide, in particular, if the polynucleotide is single stranded.

With the goal of deciphering the role of the IR/DR structure of SB transposons, the inventors have combined in vivo, in vitro and in silico approaches. They have found an orchestrated interplay between the IR/DR structure of the transposon and DNA-protein as well as protein-protein interaction surfaces of the transposase that contribute to a strictly regulated, ordered assembly of DNA-protein complexes at the ends of the transposon. They have demonstrated that, in comparison to a mariner transposon (Hsmar1), SB produces a significantly lower frequency of aberrant, single ended transposition events. Thus, the complex IR/DR structure might have evolved to protect both transposable elements as well as host cell genomes from rearrangements by suppressing aberrant transposition events.

The inventors dissected both the transposon and the transposase to small, functional domains, and addressed their contribution to the transposition process of SB. The respective experiments are described in the experimental section below. In the course of these experiments, the inventors have developed transposons comprising the new, enhanced IR/DR sequences of the invention, in particular, new DR motifs, which lead to higher transposition rates. In brief, sequences enhancing binding to the PAI domain of the Sleeping Beauty transposase were identified and tested for transposition efficiency. Surprisingly, only some of the sequences having a higher binding affinity led to an increase in transposition efficiency, in particular, the sequences of the polynucleotides of the invention described herein.

The outer DRs (also designated 14DRs or outer 14DRs) of the invention have a sequence of SEQ ID NO: 1 (left outer DR), or the inverted sequence or reverse complement thereof (right outer DR). The two variable positions in this consensus sequence, in a preferred embodiment, differ between the left outer DR and the right outer DR. Particularly, in the left outer DR, Y may be T and/or W may be A. Preferably, Y is T and W is A. Particularly, in the right outer DR, Y may be C and/or W may be T. Preferably, Y is C and W is T. Thus, preferably, the outer left DR motif comprises the nucleotide sequence of SEQ ID NO:3 and/or the outer right DR motif comprises a reverse complement of the nucleotide sequence of SEQ ID NO:4. Most preferably, the outer left DR motif comprises the nucleotide sequence of SEQ ID NO:3 and the outer right DR motif comprises a reverse complement of the nucleotide sequence of SEQ ID NO:4.

TABLE 1

Outer DRs
Differences to the sequence of U.S. Pat. No. 8,227,432 SEQ ID NO:
3 or 4 are marked in bold, novel positions are marked in bold and by
underlining. Y = C/T; W = A/T

| SEQ ID NO: | Name of sequence | Sequence |
|---|---|---|
| 13 | U.S. Pat. No. 8,227,432 outer DR SEQ ID NO: 3 | CAGTTGAAGT CGGAAGTTTA CATACACYTA AG |
| 3 | pT4/5 left outer DR | CAGTTGAAGT CGGAAGTTTA CATACACTTA AG |
| 4 | pT4/5 right outer DR | CAGTTGAAGT CGGAAGTTTA CATACACCTT AG |
| 1 | pT4/5 consensus sequence outer DR | CAGTTGAAGT CGGAAGTTTA CATACACYTW AG |

The inner DRs (also designated 12DRs or inner 12DRs) of the invention have a sequence of SEQ ID NO: 2 (left inner DR), or the reverse complement thereof (right inner DR). The three variable positions in this consensus sequence, in a preferred embodiment, differ between the left inner DR and the right inner DR. Preferably, in the left inner DR, Y is T and/or in the right inner DR, Y is C. Preferably, in the left inner DR, Y is T and in the right inner DR, Y is C. V can be A, G or C, but, preferably, V is C. K can be G or T, wherein, preferably, K is G. Thus, in one embodiment, in the left inner DR, Y is T, V is C and K is G (SEQ ID NO: 5) and/or, in the right inner DR, Y is C, V is C and K is G (SEQ ID NO: 6). Most preferably, the inner left DR motif comprises the nucleotide sequence of SEQ ID NO:5 and the inner right DR motif comprises a reverse complement of the nucleotide sequence of SEQ ID NO:6.

TABLE 2

Inner DRs

Differences to the sequence of U.S. Pat. No. 8,227,432 SEQ ID NO: 3 or 4 are marked in bold, novel positions are marked in bold and by underlining. Y = C/T; M = A/C; R = A/G; V = A/G/C, wherein V preferably is C; K = G/T, wherein K preferably is G

| SEQ ID NO: | Name of sequence | Sequence |
|---|---|---|
| 14 | U.S. Pat. No. 8,227,432 inner DR SEQ ID NO: 4 | YCCAGTGGGT CAGAAGTTTA CATACACTMA RT |
| 5 | p14/5 left inner DR | TCCAGTGGGT CAGAAGTGTA CATACACGVK CT |
| 6 | p14/5 right inner DR | CCCAGTGGGT CAGAAGTGTA CATACACGVK CT |
| 2 | p14/5 consensus sequence inner DR | YCCAGTGGGT CAGAAGTGTA CATACACGVK CT |

The inventors further found that the PAI-binding region of the DR sequences of the invention also provides an enhanced HDR region. The invention thus also provides a polynucleotide comprising a transposon of the invention, wherein the left IR/DR comprises a HDR region capable of functioning as an enhancer comprising the nucleotide sequence of SEQ ID NO:7 between the outer DR and inner DR. V can be A, G or C, wherein V preferably is C; and/or K can be G or T, wherein K preferably is G. Preferably, V is C and K is G. Optionally, the right IR/DR of said transposon further comprises a reverse complement of said HDR region.

| SEQ ID NO: 7 | HDR | GTKTA CAKACASD |
|---|---|---|

K = G/T,
S = C/G
D = A/T/G.

This preferred HDR corresponds to the PAI-binding region of the inner DR.

It is known in the prior art that the sequences surrounding the direct repeats also play an important role in the transposition efficiency of transposons. For example, the transposon is mobilized most efficiently if the number of nucleotides between outer and inner DR is about 135-196, preferably, 155-176.

Suitable framework sequences for the IR/DR of the invention can correspond to the sequences known from pT, pT2 or pT3-transposons.

The polynucleotides of the invention, which all comprise the sequences of SEQ ID NO: 1 and 2, as described herein, preferably comprise these sequences in the context of these known framework regions, or equivalent framework regions.

The invention thus provides polynucleotides, wherein the left IR/DR comprises a nucleotide sequence selected from the group consisting of SEQ ID NO: 8 and SEQ ID NO: 9 or having 90% or more sequence identity to said sequence, preferably, having 95% or more sequence identity to one of said sequences or, most preferably, from the group comprising SEQ ID NO: 8 and 9.

The invention also provides polynucleotides, wherein the right IR/DR comprises the reverse complement nucleotide sequence selected from the group consisting of SEQ ID NO: 10, SEQ ID NO:11, SEQ ID NO: 12 and SEQ ID NO: 13, and sequences having 90% or more sequence identity to one of said sequences, preferably, having 95% or more sequence identity to said sequence or, most preferably, from the group comprising SEQ ID NO: 10, 11, 12 and 13.

TABLE 3

Preferred IR/DR sequences

Left IR/DR of pT4 with HDR:

| | | |
|---|---|---|
| Left outer DR | SEQ ID NO: 1 | CAGTTGAAGT CGGAAGTTTA CATACACYTW AG |
| Left inner DR | SEQ ID NO: 2 | YCCAGTGGGT CAGAAGTGTA CATACACGVK CT |
| HDR | SEQ ID NO: 7 | GTKTA CAKACASD |
| Framework: | | pT |

SEQ ID NO: 8
TACAGTTGAAGTCGGAAGTTTACATACACYTWAGTTGGAGTCATTAAAACTCGTTTTTCAACTACTCCACAAATTTCT
TGTTAACAAACAATAGTTTTGGCAAGTCAGTTAGGACATCTACTTTGTGCATGACACAAGTCATTTTTCCAACAATTG
TKTACAKACASDTTATTTCACTTATAATTCACTGTATCACAAT<u>YCCAGTGGGTCAGAAGTGTACATACACGVKCT</u>

Left IR/DR of pT5 with HDR:

| | | |
|---|---|---|
| Left outer DR | SEQ ID NO: 1 | CAGTTGAAGT CGGAAGTTTA CATACACYTW AG |
| Left inner DR | SEQ ID NO: 2 | YCCAGTGGGT CAGAAGTGTA CATACACGVK CT |
| HDR | SEQ ID NO: 7 | GTKTA CAKACASD |

TABLE 3-continued

Preferred IR/DR sequences

Framework: pT2

SEQ ID NO: 9
TATA<u>CAGTTGAAGTCGGAAGTTTACATACACYTW</u>AGTTGGAGTCATTAAAACTCGTTTTTCAACTACTCCACAAATTT
CTTGTTAACAAACAATAGTTTTGGCAAGTCAGTTAGGACATCTACTTTGTGCATGACACAAGTCATTTTTCCAACAAT
TG<u>TKTACAKACASD</u>TTATTTCACTTATAATTCACTGTATCACAAT<u>YCCAGTGGGTCAGAAGTGTACATACACGVKCT</u>

Right IR/DR of pT4 without HDR (right IR/DR comprises the reverse complement of the given sequences):

Right outer DR    SEQ ID NO: 1    CAGTTGAAGT CGGAAGTTTA CATACACYTW AG

Right inner DR    SEQ ID NO: 2    YCCAGTGGGT CAGAAGTGTA CATACACGVK CT Framework: pT SEQ ID NO: 10
TA<u>CAGTTGAAGTCGGAAGTTTACATACACYTW</u>AGCCAAATACATTTAAACTCACTTTTTCACAATTCCTGACATTTAA
TCCGAGTAAAGATTCCCTGTCTTAAGGTCAGTTAGGATCACCACTTTATTTTAAGAATGTGAAATATCAGAATAATAG
TAGAGAGAATGATTCATTTCAGCTTTTATTTCTTTCATCACATT<u>YCCAGTGGGTCAGAAGTGTACATACACGVKCT</u>

Right IR/DR of pT5 without HDR (right IR/DR comprises the reverse complement of the given sequences):

Right outer DR    SEQ ID NO: 1    CAGTTGAAGT CGGAAGTTTA CATACACYTW AG

Right inner DR    SEQ ID NO: 2    YCCAGTGGGT CAGAAGTGTA CATACACGVK CT Framework: pT2

SEQ ID NO: 11
TATA<u>CAGTTGAAGTCGGAAGTTTACATACACYTW</u>AGCCAAATACATTTAAACTCACTTTTTCACAATTCCTGACATTT
AATCCTAGTAAAAATTCCCTGTCTTAGGTCAGTTAGGATCACCACTTTATTTTAAGAATGTGAAATATCAGAATAATA
GTAGAGAGAATGATTCATTTCAGCTTTTATTTCTTTCATCACATT<u>YCCAGTGGGTCAGAAGTGTACATACACGVKCT</u>

Right IR/DR of pT4 with HDR (right IR/DR comprises the reverse complement of the given sequences):

Right outer DR    SEQ ID NO: 1    CAGTTGAAGT CGGAAGTTTA CATACACYTW AG

Right inner DR    SEQ ID NO: 2    YCCAGTGGGT CAGAAGTGTA CATACACGVK CT

HDR               SEQ ID NO: 7    GTKTA CAKACASD

Framework: pT

SEQ ID NO: 12
TA<u>CAGTTGAAGTCGGAAGTTTACATACACYTW</u>AGCCAAATACATTTAAACTCACTTTTTCACAATTCCTGACATTTAA
TCCGAGTAAAGATTCCCTGTCTTAAGGTCAGTTAGGATCACCACTTTATTTTAAGAATGTGAAATATCAGAATAATAG
TAGAGAGAATGAT<u>GTKTACAKACASD</u>TCATTTCAGCTTTTATTTCTTTCATCACATT<u>YCCAGTGGGTCAGAAGTGTA
CATACACGVKCT</u>

Right IR/DR of pT5 with HDR (right IR/DR comprises the reverse complement of the given sequences):

Right outer DR    SEQ ID NO: 1    CAGTTGAAGT CGGAAGTTTA CATACACYTW AG

Right inner DR    SEQ ID NO: 2    YCCAGTGGGT CAGAAGTGTA CATACACGVK CT

HDR               SEQ ID NO: 7    GTKTA CAKACASD

Framework: pT2

SEQ ID NO: 13
TATA<u>CAGTTGAAGTCGGAAGTTTACATACACYTW</u>AGCCAAATACATTTAAACTCACTTTTTCACAATTCCTGACATTT
AATCCTAGTAAAAATTCCCTGTCTTAGGTCAGTTAGGATCACCACTTTATTTTAAGAATGTGAAATATCAGAATAATA
GTAGAGAGAATGAT<u>GTKTACAKACASD</u>TCATTTCAGCTTTTATTTCTTTCATCACATT<u>YCCAGTGGGTCAGAAGTGT
ACATACACGVKCT</u>

Y = C/T, wherein Y preferably is T in the left DRs and C in the right DRs;
W = A/T, wherein W preferably is A in the left DRs and T in the right DRs;
V = A/G/C, wherein V preferably is C;
K = G/T, wherein K preferably is G;
S = C/G,
D = A/T/G.
Most preferably, Y is T in the left DRs and C in the right DRs; W is A in the left DRs and T in the right DRs; V is C; S is C, D is G and K is G.

In a preferred embodiment of the polynucleotide of the invention, the left IR/DR comprises the nucleotide sequence of SEQ ID NO: 8 and the right IR/DR comprises the reverse complement nucleotide sequence of SEQ ID NO: 10 or SEQ ID NO:12. In these polynucleotides, the framework region corresponds to pT, and the polynucleotide of the invention is designated pT4.

In another preferred embodiment, the left IR/DR comprises the nucleotide sequence of SEQ ID NO: 9 and the right IR/DR comprises the reverse complement nucleotide sequence of SEQ ID NO: 11 or SEQ ID NO:13. In these polynucleotides, the framework region corresponds to pT2, and the polynucleotide of the invention is designated pT5.

The transposon of the invention is capable of being mobilized by a Sleeping Beauty transposase protein. Accordingly, the transposon is able to excise from a donor polypeptide, for instance, a vector and integrate into a target site, for instance, a cell's genomic or extrachromosomal DNA. A polynucleotide of the invention can be RNA or DNA. It can be double stranded or single stranded, or a combination thereof. Polynucleotides of the invention can be single stranded, e.g., if they are integrated in a single stranded, e.g., retroviral vector. Typically, the polynucleotides of the invention will be double stranded.

The polynucleotide of the invention may be linear or circular. Preferably, it is in circular form. It has been shown that supercoiled plasmid forms have particularly high transposition efficiency. In circular forms, for optimal efficiency, the 5' end of the left IR/DR is separated from the 3' end of the right IR/DR by a spacer, which may comprise, e.g., about 300 bp or more.

The polynucleotide may be a vector selected from the group consisting of
  (i) a viral vector selected from the group comprising an adenoviral, adeno-associated viral, lentiviral, retroviral, herpes simplex viral, baculovirus, Epstein-Barr viral, and poxvirus vector; or
  (ii) a non-viral vector selected from the group comprising a plasmid, a minicircle, a pFAR construct or a virosome.

Minicircles are small circular plasmid derivatives that have been largely or completely freed from non-essential prokaryotic vector parts. In particular, minicircles do not contain DNA encoding for bacterial genes like antibiotic resistance or the ORI. The minicircle DNA of the invention may be prepared according to Kay et al., 2010, Nature Biotechnology 28, 1287-1289. Its backbone (i.e., without cargo) preferably comprises less than 2 kb or less than 1 kb, e.g., about 540-580 bp, preferably, about 560 bp. The vector may also be a pFAR vector (plasmid free of antibiotic resistance markers), e.g., according to Marie et al, 2010, J Gen Med 12(4), 323-332).

Appropriate vectors are also described in Narayanavari et al., 2017, Crit Rev Biochem Mol Biol. 52(1):18-44; Richter et al., 2016, Blood 128(18):2206-2217; Boehme, et al., 2016. Mol Ther Nucleic Acids 5, e337; or Yant et al., 2002, Nat Biotechnol 20, 999-1005.

The polynucleotide of the invention comprises a cargo nucleic acid. Optionally, the cargo nucleic acid comprises an open reading frame operably linked to a promotor, wherein the open reading frame may encode, e.g., a T-cell receptor construct or a fragment thereof. Alternatively or additionally, the cargo nucleic acid may comprise sequences encoding at least one miRNA or shRNA. The open reading frame may alternatively or additionally encode a marker, e.g. an antibiotic resistance gene, an enzyme or a fluorescent protein. The transposon of the invention may also be suitable for insertional mutagenesis.

The invention also provides a kit for transposing a nucleic acid, wherein the kit comprises
  (i) the polynucleotide of the invention;
  (ii) (a) a SB transposase protein or (b) a nucleic acid encoding a SB transposase protein; and
  (iii) optionally, at least one cofactor selected from the group comprising
    (A) a cofactor capable of depleting a component of the FACT complex selected from the group consisting of SSRP1 and SUPT16H/SPT16;
    (B) an inhibitor of cathepsin selected from the group comprising F, H, L, S, and V; (e.g. E64D)
    (C) a cofactor capable of depleting or inhibiting HSP90 (HSPAA1), the inhibitor selected from the group comprising geldanamycin, radicicol or 17-N-Allylamino-17-demethoxygeldanamycin;
    (D) a factor temporally arresting cells cell cycle in cell cycle phase G0/G1, G1/S, or G2/M; and
    (E) a factor inhibiting the ubiquitination of PCNA (Proliferating Cell Nuclear Antigen),
    (F) an agent capable of increasing the concentration and/or the signaling of ATR (Ataxia telangiectasia and Rad3 related),
    wherein said cofactor is selected from the group comprising a small molecule, siRNA and miRNA,
    or a cell wherein
    (AA) said component of the FACT complex; and/or
    (BB) said cathepsin; and/or
    (CC) said HSP90, (HSPAA1) is knocked down; and/or
    (DD) cell cycle is temporally arrested in cell cycle phases G0/G1, G1/S, or G2/M; and/or
    (EE) the ubiquitination of PCNA is inhibited; and/or
    (FF) concentration and/or signaling of ATR is increased.

The polynucleotide comprising the transposon and the nucleic acid encoding a SB transposase protein may be located on the same vector or on different vectors, in particular, if the nucleic acid encoding the SB transposase protein is DNA. If said nucleic acid encoding the SB transposase protein is RNA, the polynucleotide comprising the transposon typically is in DNA form, preferably in a circular, most preferably supercoiled form. Often, the polynucleotide comprising the transposon will be in DNA form, preferably in a circular, most preferably, supercoiled form, and the SB transposase will be in protein form.

Optionally, the kit further comprises suitable buffers or cell culture mediums, and/or instructions for transfecting cells and/or producing recombinant nucleic acids. The transposition may be carried out in vitro, e.g., according to the method taught by Goryshin et al., 1998, JBC 273, 7367-7374. Usually, however, the transposition occurs in cells, typically in cell culture or ex vivo. Microinjecting single cell zygotes followed by implantation into a superovulated female is possible. In addition, the transposition can occur in vivo in conjunction with hybrid SB-viral vectors (e.g. hybrid SB-adeno such as Zhang et al, 2013 PLoS One 8(10): e75344) or by electroporation or nanoparticle delivery.

In all embodiments of the invention, the SB transposase may be, e.g., an SB transposase disclosed by U.S. Pat. No. 8,227,432 B2, or SB10 (Ivics et al., 1997, Cell 91:501-510). Preferably, throughout the invention, it is hyperactive transposase SB100X (Mátés L1, et al. Molecular evolution of a novel hyperactive Sleeping Beauty transposase enables robust stable gene transfer in vertebrates. Nat Genet. 2009 June; 41(6):753-61).

The inventors have further surprisingly found that the efficiency of transposition is significantly increased if at least one cofactor as described above is present during transposition, in particular, (A) a cofactor capable of depleting a component of the FACT complex, or alternatively, (B) an inhibitor of lysosomal cathepsin selected from the group comprising F, H, L, S, and V; (C) a cofactor capable of depleting HSP90; or (D) a factor temporally arresting cells cell cycle in cell cycle phase G0/G1, G1/S, or G2/M; or (E) a factor inhibiting the ubiquitination of PCNA; or (F) an agent capable of increasing the concentration and/or the signaling of ATR.

In mammalian cells, SSRP1 and SUPT16H/SPT16 exist as a heterodimer, and are components of Facilitates chromatin transcription (FACT) complex. FACT complex is involved in various processes such as DNA replication and repair. Depletion of FACT homolog in *Xenopus* resulted in defective replication (Orphanides et al., 1999, Nature 400: 284-288) indicating a role in replication. In addition, it has also been shown that FACT complex can interact with proteins involved DNA damage repair processes such as PARP1 and RPA (Huang et al., 2006, Nucleic Acids Res. 34:2398-2407; VanDenmark et al., 2006, Mol Cell. 22:363-374; Solinger et al., 2002, Mol Cell. 10:1175-1188). Recently, it has been shown that depletion of SSRP1 resulted in enhanced homologous recombination activity and increased formation of H2AX and Rad51 foci. Interestingly, it was also shown that SSRP1 can physically interact with Rad54 and functionally inhibit the BM activity of HJs promoted by Rad54 in vitro (Kumari et al., 2009, J Cell Biochem. 108:508-518).

Accordingly, the at least one cofactor capable of depleting a component of the FACT complex is capable of depleting SSRP1 and/or SUPT16H/SPT16. Depletion has the consequence that the component in question, in particular, the component of the FACT complex, is not any more available for interaction with the transposase and/or the transposon. This can be achieved by reducing the concentration of the depleted component, e.g., the component of the FACT complex, e.g., by knockdown in a stable cell line by RNA interference, by siRNA or miRNA, or by sequestering the component of the FACT complex, e.g., with a suitable antibody to SSRP1 or SUPT16H/SPT16.

Preferably, the cofactor is selected from the group comprising a small molecule, an antibody, shRNA, siRNA and miRNA. The small molecule may be an active agent of up to about 800 g/mol. For example, a cathepsin inhibitor such as E64D may be used. A HSP90 inhibitor such as geldanamycin, radicicol or 17-N-Allylamino-17-demethoxygeldanamycin may alternatively or additionally be used.

The inventors could show that depletion of SUPT16H leads to the strongest increase in transposition, and is thus preferred.

Cofactors capable of depleting the components in question, for example, SSRP1 and/or SUPT16H/SPT16 can e.g., be identified by a binding assay, or a transposition assay as described below. siRNA and miRNA capable of reducing the concentration of SSRP1 or SUPT16H/SPT16 can be prepared by the skilled person, and are available commercially. Pre-designed, commercial, synthetic, siRNAs (siGENOME, SMARTpool) were procured (from Dharmacon, GE healthcare). siRNAs targeting either supt16H gene (cat. No. M-009517-00-0005) and ssrp1 (cat. No. M-011783-01-0005) were transfected into Hek293T using jetPEI™ transfection system. As a negative control siRNA targeting firefly luciferase gene (cat. No. D-001206-14-05) was used. For miRNA based knockdown, miRNAs targeting the genes (Table 5) were synthesized (Eurofins) and eventually cloned into miRNA vector before transfection.

Both components of the FACT complex can be depleted, but the inventors could show that depletion of one of the components is already sufficient to increase transposition efficiency significantly, e.g., by a factor of about 50. This applies both for transposition using, e.g., non-hyperactive SB10 and SB100X.

Depletion of at least one component of the FACT complex increases transposition efficiency of the transposon of the present invention (e.g.,pT 4 or pT5) as well as other transposons, in particular Tc1/mariner type transposons, e.g., Sleeping Beauty transposons such as pT, pT2, or pT3.

Figure 6A:
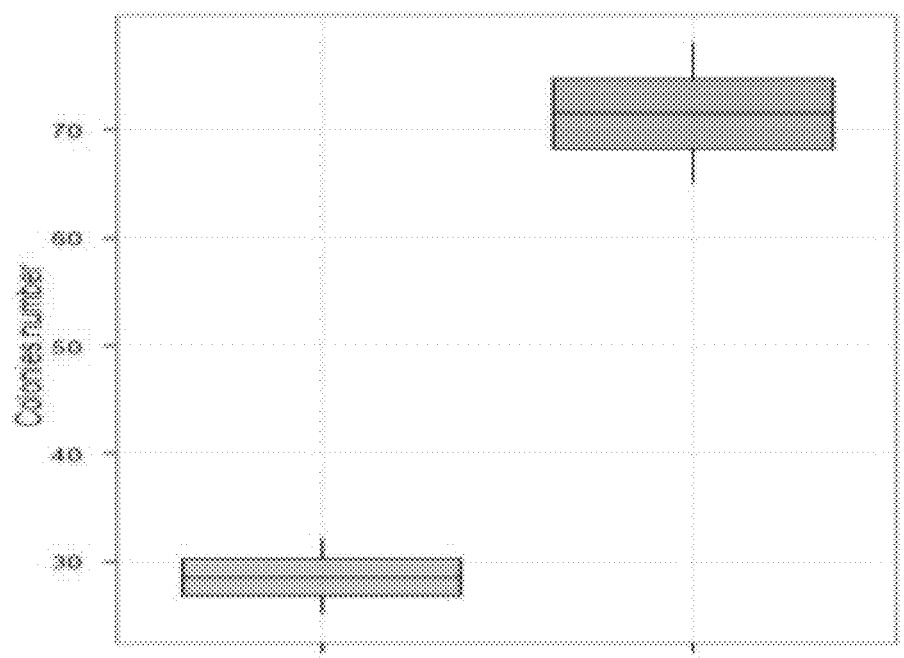
Figure 6B:
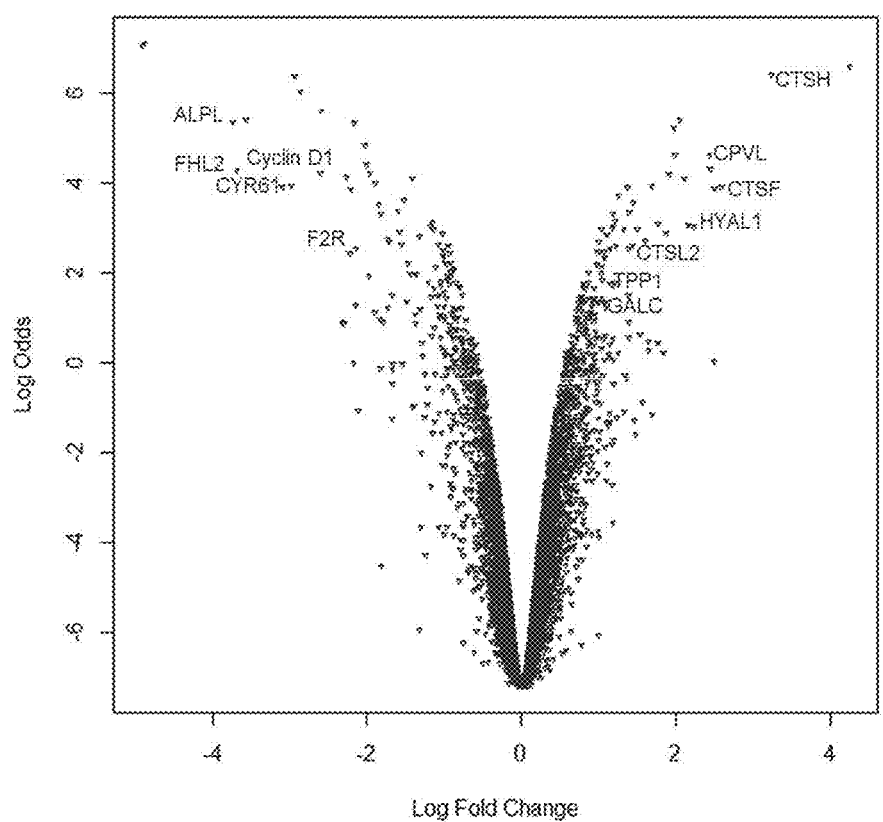

In order to monitor transcriptional changes activated by the transposase, a genome-wide transcriptional study was performed (HeLa, Affymetrix). The transcriptome analysis revealed that several host-encoded genes are regulated differently in the presence of the transposase. The list of upregulated proteins includes HSAP2 alias HSP70-2 and several members of the cathepsin family (FIG. 6A). While HSPA2, a variant of the heat shock protein HSP70, is a member of the stress response, cathepsins are lysosomal proteases and have a vital role in mammalian cellular turnover. Preliminary results suggest that modulating the stress response by inhibiting HSP90 (HSP90AA1) or inhibiting cathepsin activity (FIG. 6B) improves SB transposition. In addition, by mitigating the cellular stress response induction of the apoptotic signalling is moderated and cell viability improved.

Figure 7A:
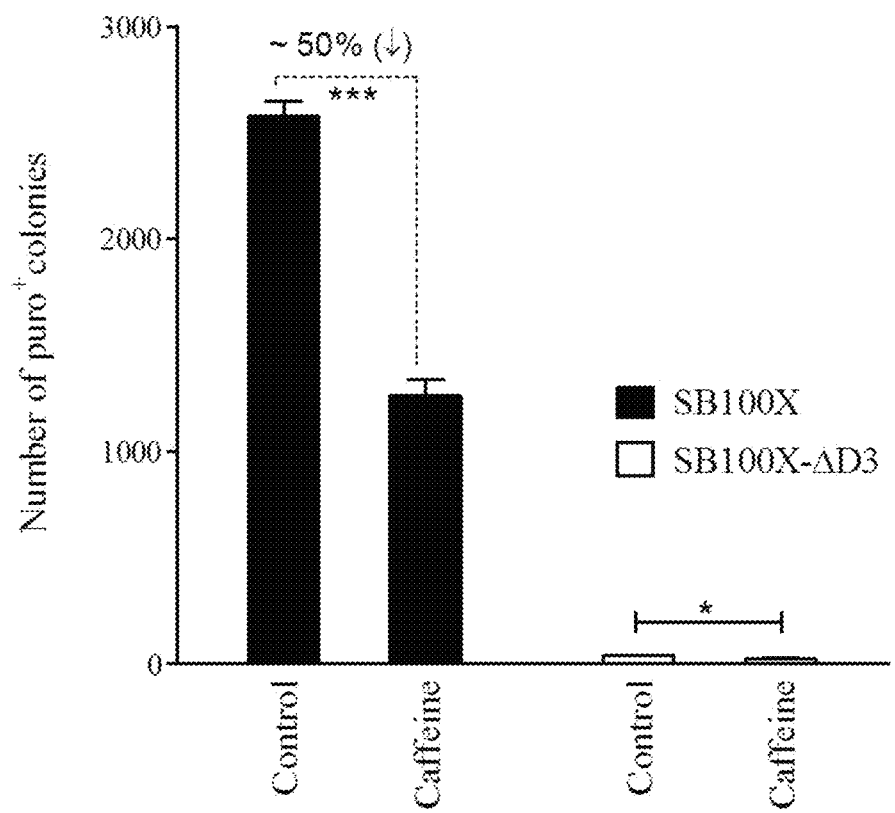
Figure 7A:
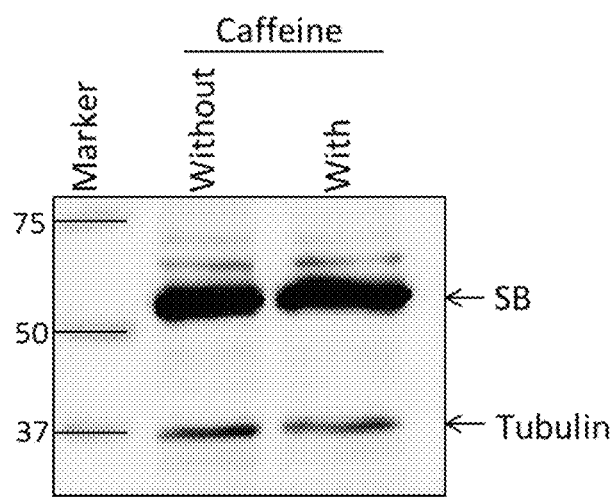

The inventors have further shown that transposition via Sleeping Beauty, e.g., of the transposon of the invention described herein or conventional Sleeping Beauty transposons such as pT2, requires ATR signalling (Example 2 and FIG. 7). Accordingly, an agent capable of increasing the concentration and/or the signaling, preferably, the concentration, of ATR can thus advantageously be comprised in a kit of the invention. Preferably, the agent increases expression of ATR. Such an agent may, e.g., be a polynucleotide encoding ATR, e.g., an mRNA. A polynucleotide encoding ATR may also be DNA, e.g., in a form suitable for integration into the genome of a cell. Alternatively, ATR may be encoded on the polynucleotide of the invention, preferably, outside the region flanked by the left and right inverted repeat/direct repeat The agent may also be ATR in protein form. A cell wherein concentration and/or signaling of ATR is increased preferably comprises such an agent. Preferably, expression of ATR is increased. An increase in this context relates to the comparison to a cell wherein concentration or signaling of ATR have not been influenced by addition of such an agent.

Alternatively, an agent capable of decreasing the concentration and/or the signalling of ATR, preferably, signalling, can be comprised in a kit of the invention, if regulation of Sleeping Beauty activity is desired, e.g., as a negative control wherein Sleeping Beauty activity is negatively regulated. An agent capable of decreasing the concentration of ATR may be miRNA. An agent capable of decreasing the signalling of ATR may be caffeine.

The invention thus provides a method of preparing a recombinant polynucleotide or a recombinant cell comprising a recombinant polynucleotide by transposition of a transposon, preferably, a Sleeping Beauty transposon, wherein at least one cofactor or agent as described above, e.g., a cofactor capable of depleting a component of the FACT complex, is present. The cofactor or agent can be introduced into a cell, preferably, in vitro or ex vivo.

The invention also provides use of a at least one cofactor or agent as described above, e.g., a cofactor capable of depleting a component of the FACT complex, for preparing a recombinant polynucleotide or a recombinant cell comprising a recombinant polynucleotide by transposition of a transposon, preferably, a Sleeping Beauty transposon, wherein the transposition efficiency is significantly increases compared to the same conditions without said cofactor or agent. Preferably, transposition is increased by a factor of at least about 10, at least about 20, at least about 30, at least about 40 or at least about 50.

The invention also provides knockdown cells, e.g., cell lines, for SSRP1 and/or SUPT16H/SPT16 (ΔSSRP1 or ΔSUPT16H/SPT16), e.g., on the basis of HEK293T cells (HEK293T ΔSSRP1 and HEK293T ΔSUPT16H/SPT16), and their use for generating a recombinant polynucleotide or recombinant cell by transposition, preferably, transposition employing Sleeping Beauty transposons such as pT2. Knockdown cell lines for HSP90 and/or cathepsin and/or cells wherein ubiquitination of PCNA is inhibited and/or cell cycle arrested in one of the stages described above can also be used. Such cell lines may be a component of a transposition kit such as the kit of the invention. Such cell lines can be used to achieve high transposition efficiencies. Preferably, such knockdown cells are stable cell lines.

A knockdown cell line of the invention may be a cell line modified to comprise a reduced concentration of a component of the FACT complex. Said reduction can occur through genetic modification or by treatment with a reagent such as a short DNA or RNA oligonucleotide that has a sequence complementary to either gene or an mRNA transcript. If genetic modification of DNA is done, the result is a stable knockdown. If the change in gene expression is caused by an oligonucleotide binding to an mRNA or temporarily binding to a gene, this leads to a temporary change in gene expression that does not modify the chromosomal DNA, and the result is referred to as a transient knockdown.

In a transient knockdown, the binding of this oligonucleotide to the active gene or its transcripts causes decreased expression through a variety of processes. Binding can occur either through the blocking of transcription (in the case of gene-binding), the degradation of the mRNA transcript (e.g. by small interfering RNA (siRNA) or RNase-H dependent antisense), or through the blocking of either mRNA translation, pre-mRNA splicing sites, or nuclease cleavage sites used for maturation of other functional RNAs, including miRNA (e.g. by morpholino oligos or other RNase-H independent antisense) (Wikip edia).

A preferred knockdown method in the invention is RNA interference (RNAi) is a means of silencing genes by way of mRNA degradation. Gene knockdown by this method is achieved by introducing small double-stranded interfering RNAs (siRNA) into the cytoplasm. Small interfering RNAs can originate from inside the cell or can be exogenously introduced into the cell. Once introduced into the cell, exogenous siRNAs are processed by the RNA-induced silencing complex (RISC). The siRNA is complementary to the target mRNA to be silenced, and the RISC uses the siRNA as a template for locating the target mRNA. After the RISC localizes to the target mRNA, the RNA is cleaved by a ribonuclease. The siRNA can be constitutively expressed in the cell line or introduced at the same time as the other components for transfection, e.g., by electroporation.

Thus, depending on the method employed for knockdown, the cell may comprise a cofactor capable of depleting a component of the FACT complex. The invention also provides a method for preparing a recombinant polynucleotide or a recombinant cell comprising a recombinant polynucleotide by transposition of a transposon such as a Sleeping Beauty transposon, wherein the transposon preferably is the transposon of the invention described herein, comprising inducing transposition in a cell wherein, e.g., a component of the FACT complex is knocked down, e.g, by introducing a transposase (in protein or nucleic acid form) and a transposon into said cell. The invention also provides use of a cell wherein, e.g., a component of the FACT complex is knocked down for preparing a recombinant polynucleotide or a recombinant cell comprising a recombinant polynucleotide by transposition of a transposon such as a Sleeping Beauty transposon, wherein the transposon preferably is the transposon of the invention.

The invention also provides an organism (in particular, a non-human organism such as a mouse or a rat) comprising a knockdown cell of the invention, and its use in producing a transfected organism by transposition of a Sleeping beauty transposon, preferably, pT4 or pT5.

The invention also provides a method of producing a recombinant nucleic acid, comprising contacting a target nucleic acid comprising a recognition sequence for a Sleeping Beauty transposase with the components of the kit of the invention.

The invention also provides a method of producing a transfected cell, wherein the method comprises introducing into said cell the components of the kit of the invention. Preferably, the method comprises electroporating the cells. Methods of the invention may be carried out in vitro or in vivo, preferably, in vitro.

The polynucleotide and/or the kit of the invention may also be used for the generation of cell pools (i.e., polyclonal cultures of recombinant cells) and clonal cell lines for the large-scale production of recombinant proteins using, e.g., Chinese hamster ovary cells as the host. Chinese hamster ovary (CHO) cells remain the most popular host for the production of biopharmaceutical drugs, particularly monoclonal antibodies (mAbs), bispecific antibodies, and Fc-fusion proteins. Accordingly, the invention also provides a process for the production of a protein, e.g., antibodies or derivatives thereof such as bispecific antibodies or Fc fusion proteins, comprising steps wherein a polynucleotide of the invention encoding said protein is introduced, e.g., electroporated, into a host cell such as a CHO cell, preferably, using a kit of the invention, and wherein said protein is isolated.

The invention also provides a host cell comprising the polynucleotide of the invention comprising a transposon. In one embodiment, the host cell is a T cell suitable for adoptive T cell transfer which comprises a transposon of the invention, wherein the cargo nucleic acid is a transgenic TCR construct or a fragment thereof and/or encodes at least one miRNA.

The invention further provides a pharmaceutical composition comprising a host cell of the invention. For example, if the host cell expresses a transgenic T cell construct reactive with a tumor antigen, the pharmaceutical composition may be used in a method of treating cancer. In other embodiment, the host cells of the invention are suitable for treatment of an infectious, e.g., viral or bacterial disease (e.g., because they are T cells expressing an appropriate TCR construct capable of targeting infected cells).

The invention is further illustrated and explained in the appended examples, which are not intended to limit the scope of the claims. All references cited herein are fully incorporated. "A", unless explicitly stated otherwise, is meant to be understood as "at least one". "About" means+/−10%.

FIGURE LEGENDS

FIG. 1 Structure of Mariner/Tc1 and Sleeping Beauty transposable elements.

A. In mariners, the transposase coding sequence (gray cylinder) is flanked by simple terminal inverted repeats (IRs), containing a single recognition motif per IRs. B. In Sleeping Beauty, the IR/DR elements possess longer terminal IRs (arrows), with two recognition signal sequences per IRs, repeated twice in a directly repeated form (DRs). The left IR additionally carries a motif (HDR) that is functioning as an enhancer in transposition.

FIG. 2 Selection of optimal binding sites for the SB transposase by CASTing.

A. Flow chart of the CASTing strategy. B. Oligonucleotides selected by six CASTing cycles were sequenced and tested in electromobility shift assay (EMSA) using the full (PAIRED) DNA-binding domain of the SB transposase, N123 (Ivics Z, et al., 1997. Cell, 91: 501-10). Binding affinities were compared to the 14DR motif of the SB left IR. Cpx—DNA-protein complex, free—position of the free DNA probes. (Right panel). C. The complexes shown FIG. B were quantified, and relative substrate-binding affinity values were calculated. D. Sequence alignment of optimal binding sites selected by the CASTing strategy. Binding region for RED is in italic, the nucleotides for AT-hook binding are boxed and binding region for PAI is in capital. Sequences were aligned to the wild-type motifs of either 12DR (left panel) or 14DR (right panel) of the left IR of the SB transposon. The identity scores are shown below. Identical nucleotides are in coloured background (black—above 50%; gray—below 50%). 20% and 70% of the wild-type motifs were recovered by the CASTing experiment of the RED and PAI wild-type motif, respectively. Selected, optimal binding sites, used in EMSA (FIG. 3A) are labelled with a star.

WT 12DR: SEQ ID NO: 14 14DR: SEQ ID NO: 15
CAST-1 12DR: SEQ ID NO: 16 14DR: SEQ ID NO: 17
CAST-2 12DR: SEQ ID NO: 18 14DR: SEQ ID NO: 19
CAST-3 12DR: SEQ ID NO: 20 14DR: SEQ ID NO: 21
CAST-4 12DR: SEQ ID NO: 22 14DR: SEQ ID NO: 23
CAST-5 12DR: SEQ ID NO: 24 14DR: SEQ ID NO: 25
CAST-6 12DR: SEQ ID NO: 26 14DR: SEQ ID NO: 27
CAST-7 12DR: SEQ ID NO: 28 14DR: SEQ ID NO: 29
CAST-8 12DR: SEQ ID NO: 30 14DR: SEQ ID NO: 31
CAST-9 12DR: SEQ ID NO: 32 14DR: SEQ ID NO: 33
CAST-10 12DR: SEQ ID NO: 34 14DR: SEQ ID NO: 35
CAST-11 12DR: SEQ ID NO: 36 14DR: SEQ ID NO: 37
CAST-12 12DR: SEQ ID NO: 38 14DR: SEQ ID NO: 39
CAST-20 12DR: SEQ ID NO: 40 14DR: SEQ ID NO: 31

Figure 3:
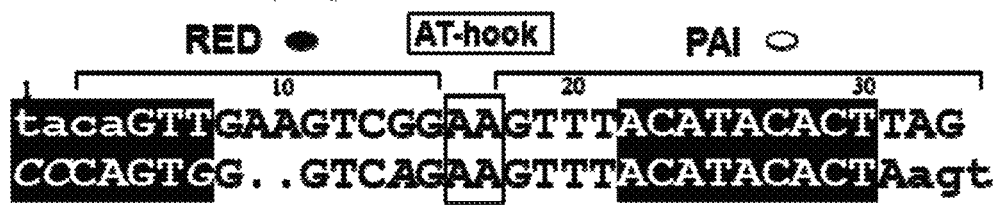
Figure 3:
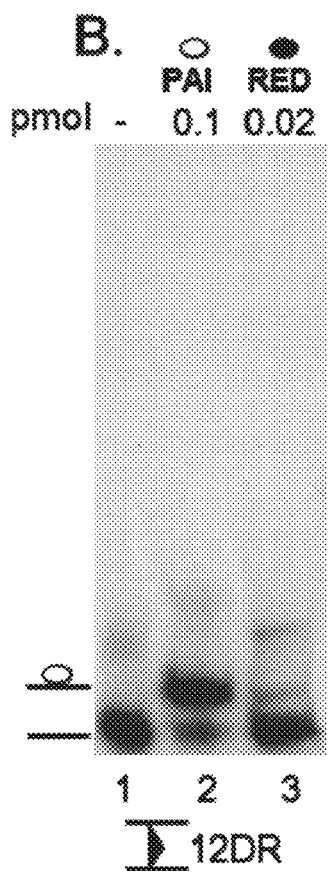
Figure 3:
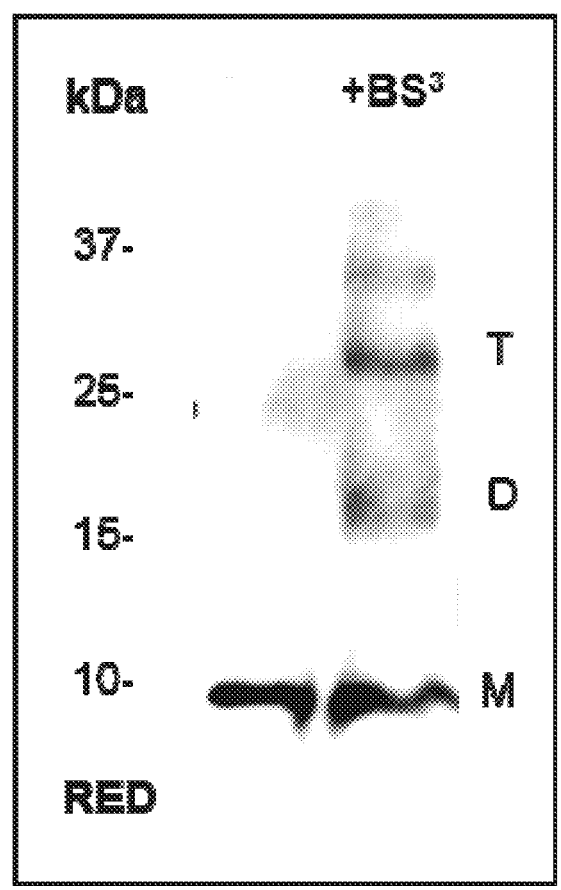
Figure 3:
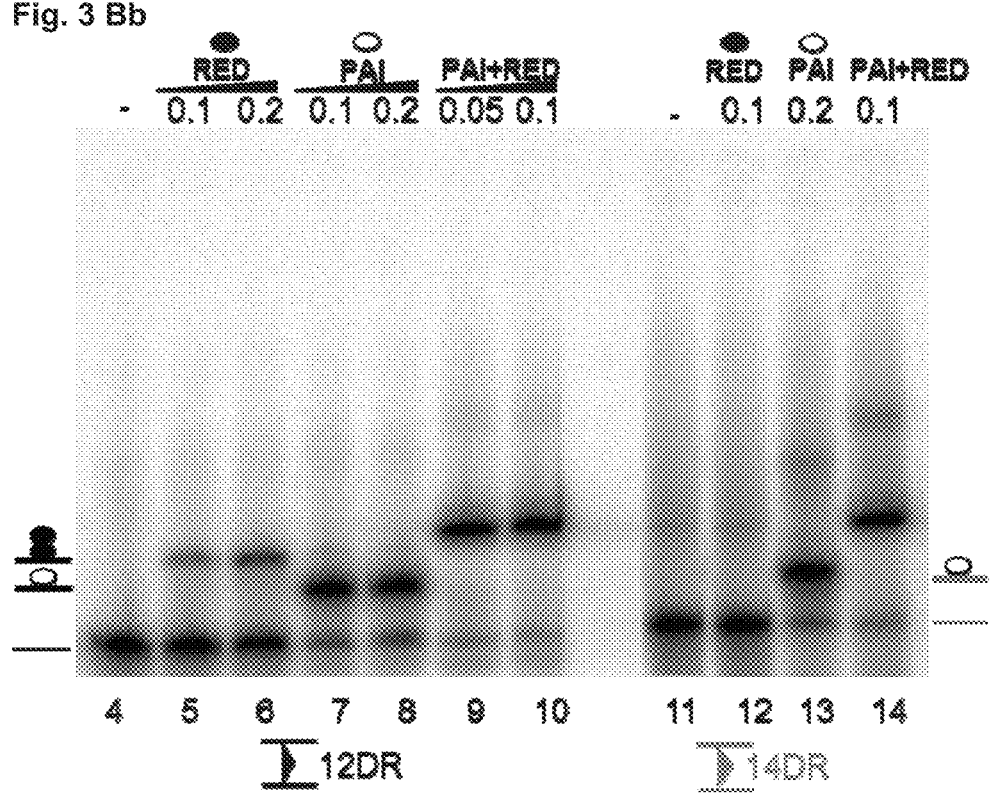
Figure 3:
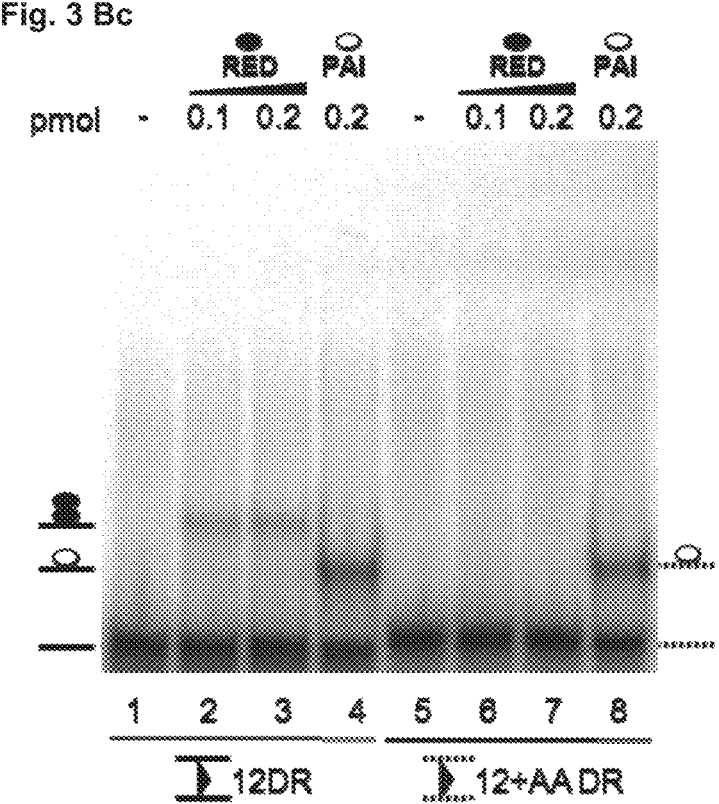

FIG. 3 Distinction between 12 vs 14 DRs is mediated by the RED subdomain of the DNA-binding domain of the SB transposase. A. Alignment of the 14 (outer) DR (SEQ ID NO:32) and 12 (inner) DR (SEQ ID NO:33) of the left inverted repeat (IR). The nucleotides involved in DNA-protein interaction, identified by footprinting (Ivics Z, et al., 1997. Cell, 91: 501-10), are shown in uppercase, while the nonidentical nucleotides are in italics. The nucleotides recognized by PAI (empty circle) or RED (black circle) subdomain, and the AT-hook (framed) are indicated (Izsvak Z, et al., 2002. Chem, 277: 34581-8.) The nucleotides resemble to the "heptamer" and "nonamer" motifs of the RAG1 are highlighted in black boxes (Hesse, J E et al., 1989. Genes Development, 3: 1053-61). The length of the spacer between motifs is 12, or 14 in the inner and outer DR, respectively.

B. DNA binding properties of RED (N58-123, black circle), PAI (N1-57, empty circle) or the full N-terminal DNA binding domain (PAI+RED) were tested by EMSA. Panels 3Ba and 3Bb: labelled oligonucleotides corresponding to the 12DR (black), the 14DR (gray) or the 12+AA DR (dotted, black) were used as DNA substrates. The schematic of the predicted nucleoprotein complexes are depicted. Complexes formed with the full N-terminal DNA binding domain (PAIRED, N123) were used as size markers (~2×RED). The complexes were separated on 4% (panel 3Ba) or 6% (panels § Bb and 3Bc) native gels. C. Oligomerization properties of the RED subdomain in the presence of a chemical cross-linker, 2 mM BS3. The complexes were separated by 15% SDS-PAGE, followed by Western blotting, using polyclonal antibody against SB transposase. Expected molecular masses of the complexes (histidine tags inclusive) are as follows: -M (REDmonomer) 8.5 kDa; -D (REDdimer) 17 kDa; -T (REDtetramer) 34 kDa.

Figure 4:
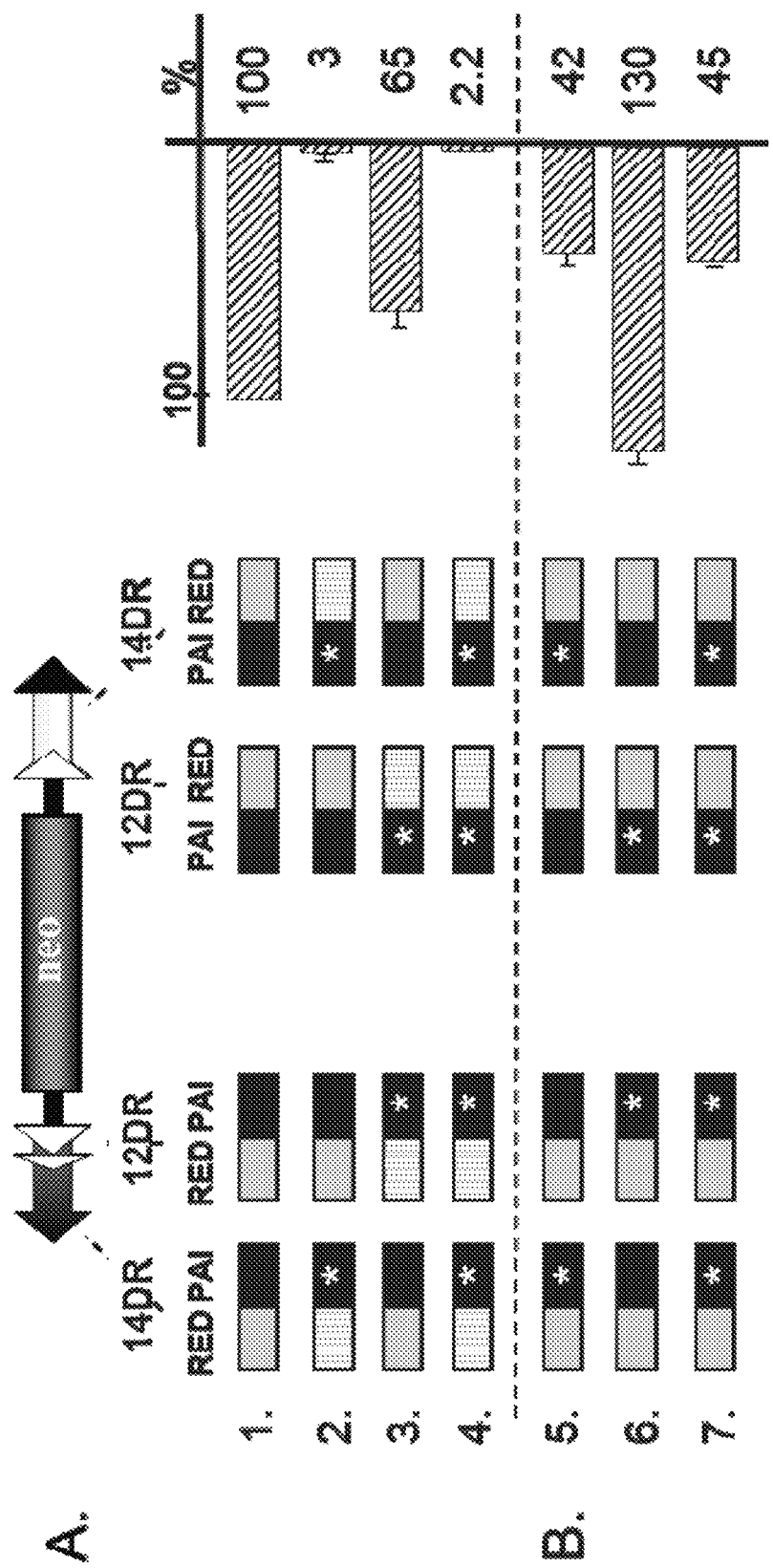

FIG. 4 Enhanced binding affinity at the inner DR improves Sleeping Beauty transposition. On the left, schematics of various neo-marked, mutated transposon constructs are depicted. On the right, the respective transpositional activities are shown in comparison to wild type transposon (construct 1), set as 100%. A. Composite DRs were created by changing either the PAI (black box) or the RED (grey box) recognition motifs into a high-affinity binding site (CAST-5) selected by the CASTing experiment (marked by stars at the PAI and stripped at the RED recognition motifs). B. The CAST-5 sequence (SEQ ID NO: 24 or 25) was used to replace only the PAI recognition motif, while the rest of the DR was wild type.

Figure 5A:
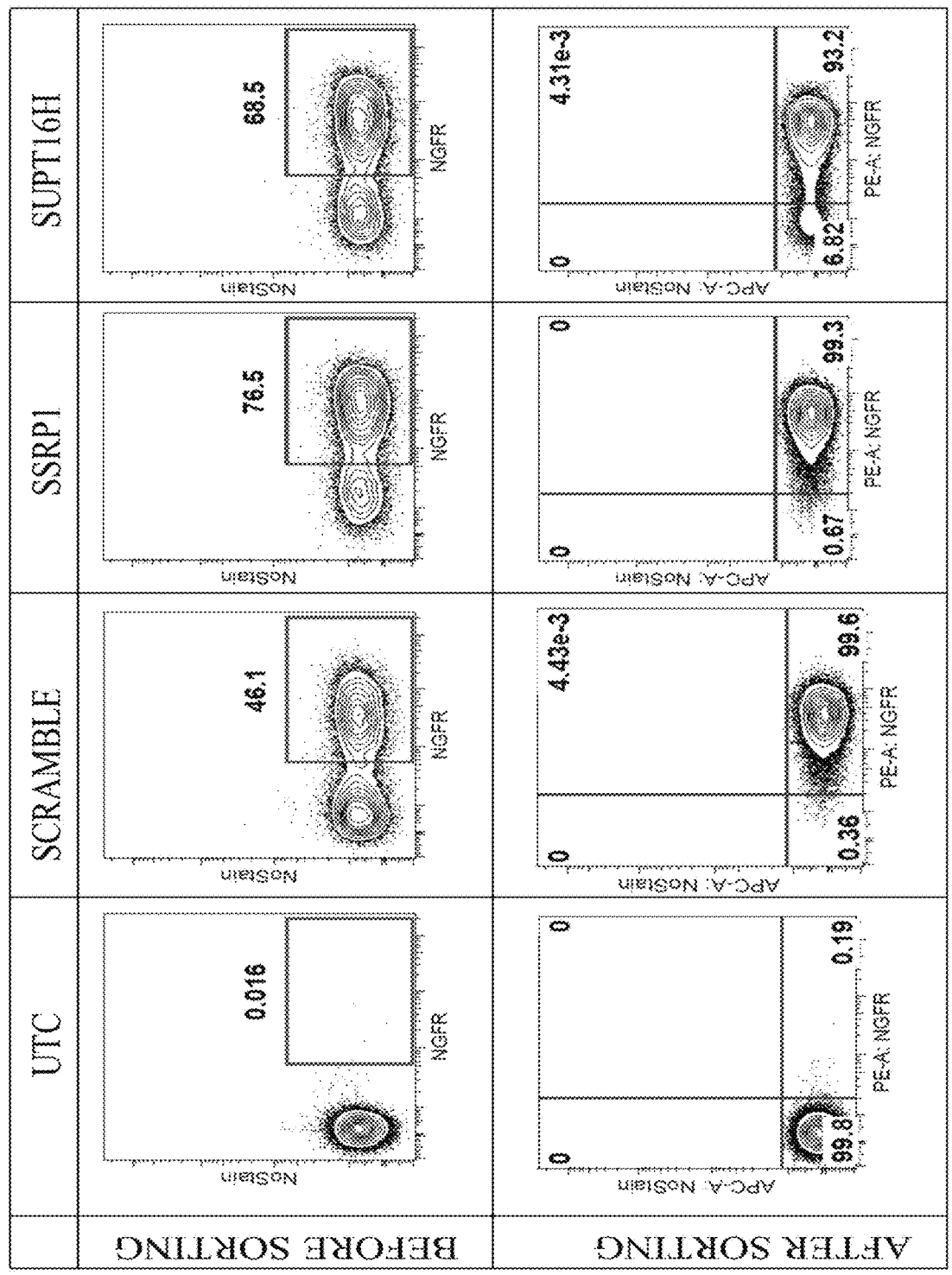
Figure 5:
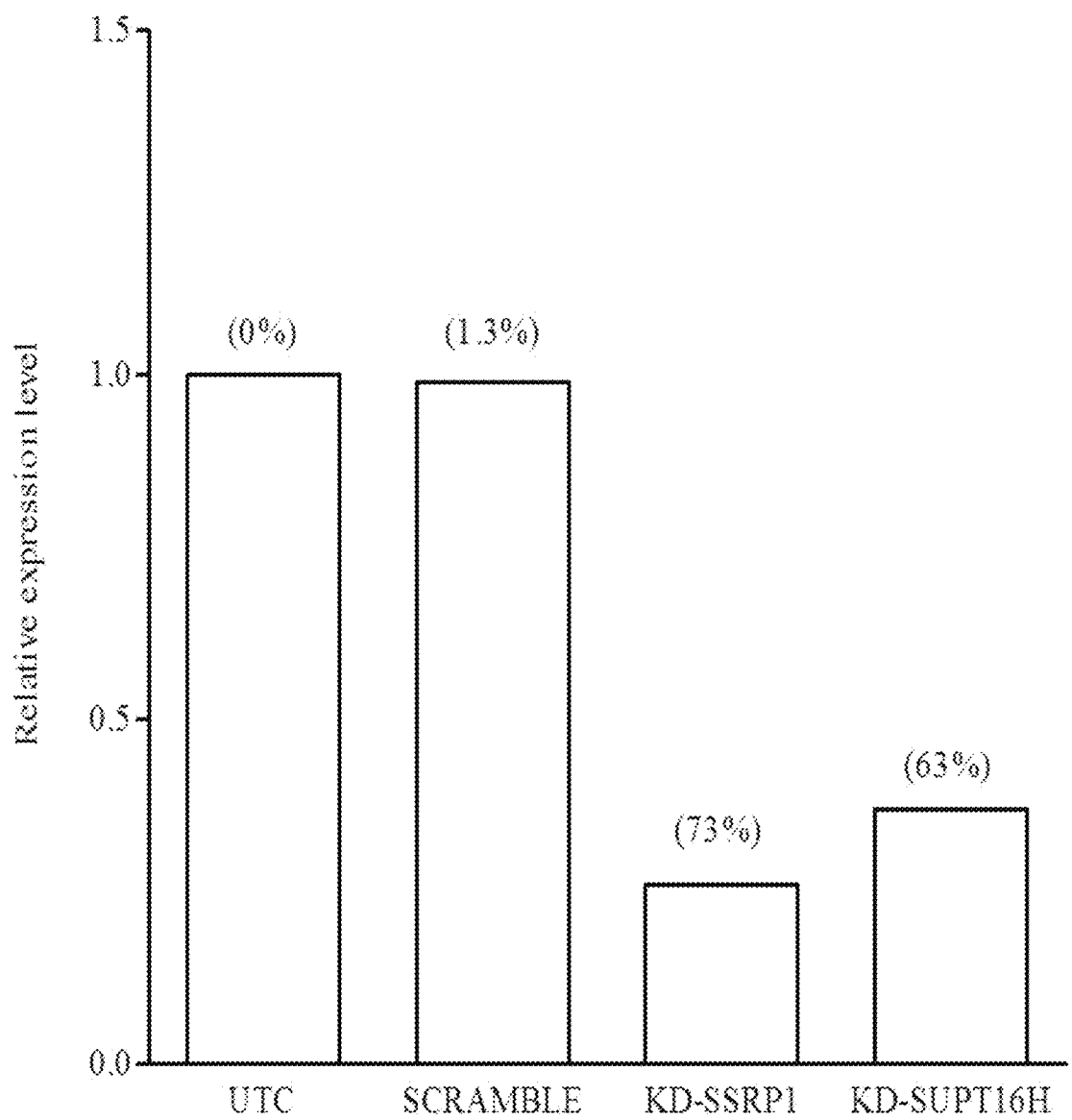
Figure 5C:
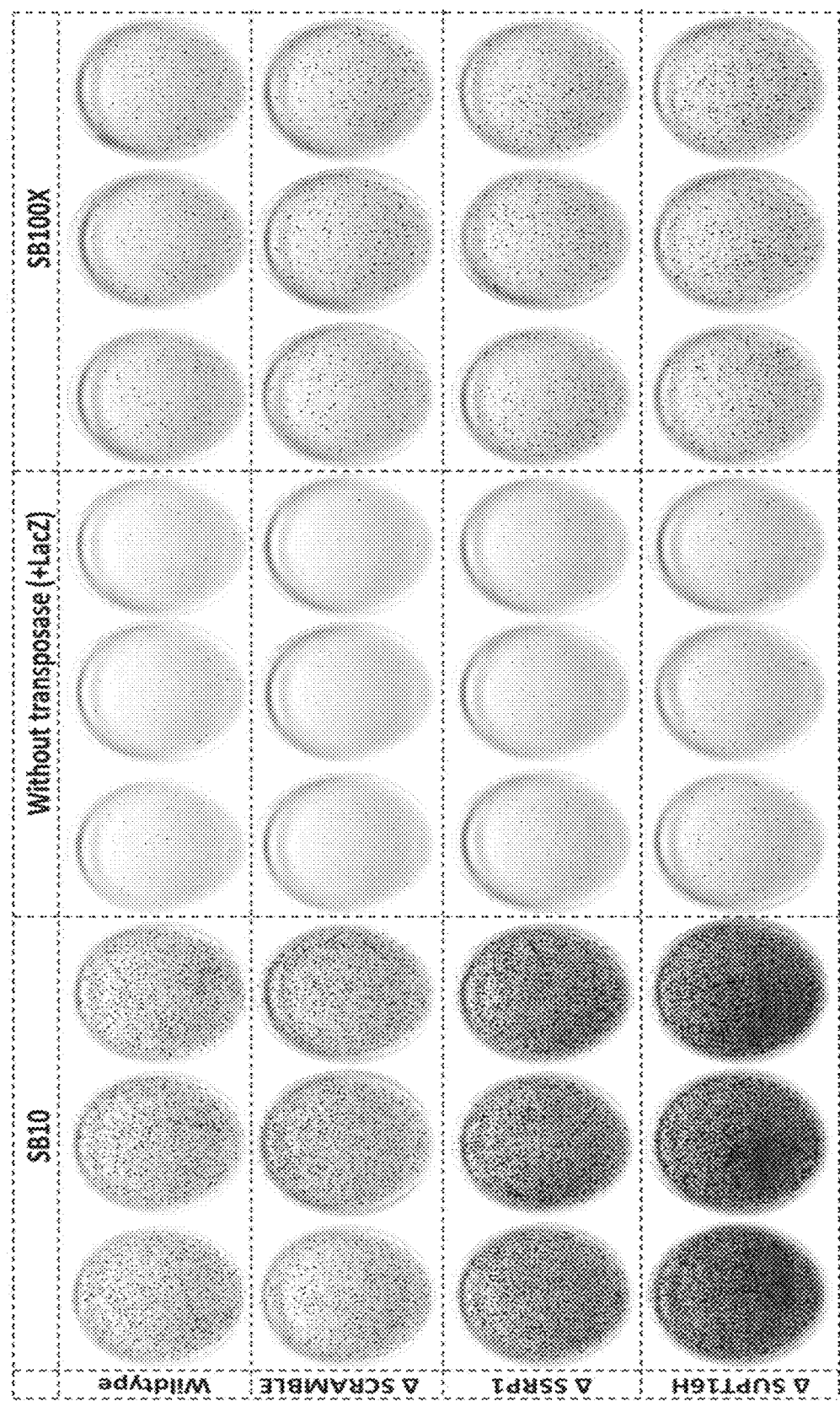
Figure 5D:
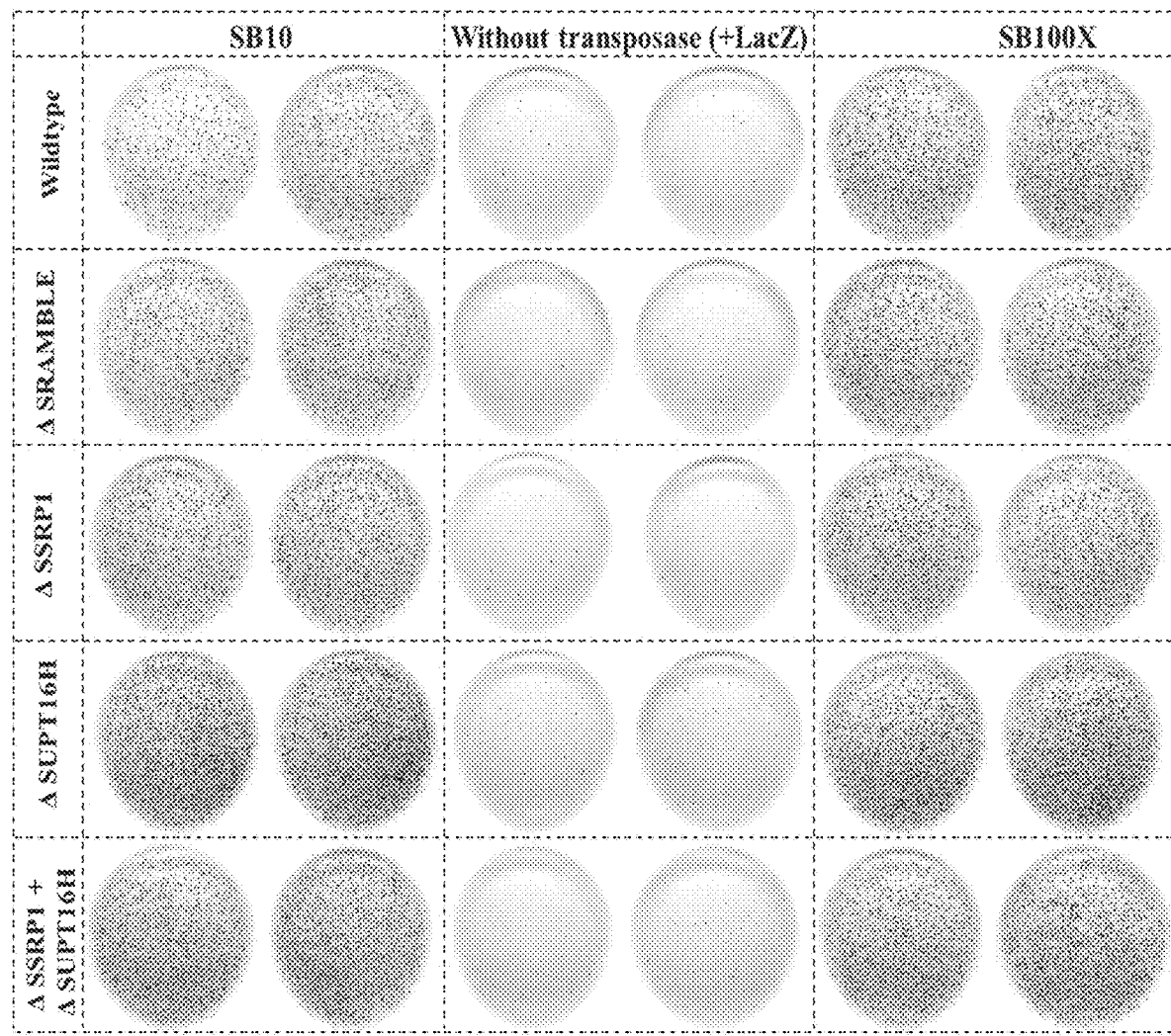

FIG. 5 Transposition assay in stable knockdown cell lines, generated by RNA interference.

A. Enrichment of cells having the knockdown construct. Hek293T cells were untransfected, transduced with a retroviral vector MPSV-LTR—Intron—truncated hNGFR—WPRE—miRNA—LTR as further detailed in the experimental part, wherein the miRNA was as follows: construct that is not targeting any host gene is used as negative control (scramble), or miRNA constructs having 21 nucleotides (nt) specifically targeting either ssrp1 or supt1 6H. Surface NGFR expression of transduced Hek293T cells was monitored by flow cytometry (after transduction), x axis. y axis: no stain. For enriching cell population expressing miRNAs, cells were FACS sorted and analyzed again (after sorting). The data shows increased expression of NGFR when miRNA depleting components of the FACT complex is present.

B. Knockdown efficiency of the miRNA was monitored by qPCR from miRNA enriched cell population. Numbers shown in parenthesis above the bars represent the % of knockdown.

C. Transposition assay in knockdown cell lines. Petri dishes with stained colonies of puromycin-resistant Hek293T cells that have been transfected with either pCMV-SB10 & pT2B-Puro or pCMV-LacZ & pT2B-Puro or pCMV-SB100x & pT2B-Puro.

D. Transposition assay in HEK293T cells using transient transfection with siRNA. The siRNA target either ssrp1 or supt1 6H. scrambled riRNA not targeting any gene is used as negative control. Petri dishes with stained colonies of puromycin-resistant Hek293T cells that have been transfected either with pCMV-SB10 & pT2B-Puro or pCMV-LacZ & pT2B-Puro or pCMV-SB100x & pT2B-Puro.

FIG. 6 A. Effect of E64D (an inhibitor of cathepsins, cystein proteases and calpain) on SB transposition. Transposition assay, (20 µM, right side; control, left side). RNAi approach against cathepsin(s) is expected to yield a similar improvement. B. Differential expression of host genes in the presence oft the transposase (HeLa, Affymetrix). Down-regulated host genes (right side), upregulated host genes (left side). Cathepsins (CTs) degrade polypeptides and are distinguished by substrate specificities (CTSH, CTSF, CTS2).

FIG. 7 A. Caffeine treatment inhibits SB transposition. HeLa cells were exposed to the ATR signalling inhibitor caffeine (4 mM) treatment at the time of transfection with transposon (250 ng of pT2B-Puro) and transposase (25 ng of pCMV-SB100x) or D3 transposase (25 ng of catalytically inactive pCMV-SB100x) plasmids. Cells were harvested 24 hours after treatment and subjected for colony forming assay, cell cycle analysis and western blot. (i) Bar graph showing the results of colony forming assay. (ii) Western blot showing the expression levels of SB transposase in un-treated and caffeine treated cells. Expression levels of tubulin are shown as loading controls. * P>0.05 (considered not significant); *** P<0.001 (one-way ANOVA, Tukey-Kramer Multiple Comparisons post-test).

B. ATR compromised cells are defective in SB transposition. SB transposition was monitored in stable cell lines expressing either ATR or ATRkd (a dominant negative kinase-inactive allele of ATR) in an inducible manner. Bar graph showing the results of colony forming assay from ATR wildtype and ATRkd cells. Transposition was severely affected in ATR disabled cells.

EXAMPLES

Example 1

Results

PAI Subdomain of the SB Transposase Mediates Primary Substrate Contact

The DRs of the IR/DR have a composite structure, recognized by a composite DNA-binding domain. The DNA-binding domains of the SB transposase consist of two helix-turn-helix (HTH) motifs, referred as PAI and RED, based on their resemblance to the PAIRED domain, present in the PAX family of transcription factors (Izsvak Z, et al., 2002J Biol Chem, 277: 34581-8.; Czerny T, et al., 1993. Genes Dev., 7: 2048-61.). Both subdomains are involved in sequence-specific DNA-binding: PAI binds the 3'- and RED interacts with the 5'-part of the bipartite transposase binding sites represented by the DRs (Izsvak Z, et al., 2002. J Biol Chem, 277: 34581-8). In addition to DNA binding, PAI was previously shown to have a protein-protein interaction interface (Izsvak Z, et al., 2002. J Biol Chem, 277: 34581-8.). Notably, the four DRs of SB are not identical, as the DRs at the transposon ends (outer DRs) are longer by 2 bps (14DRs vs 12DRs in FIG. 1A).

Figure 2A:
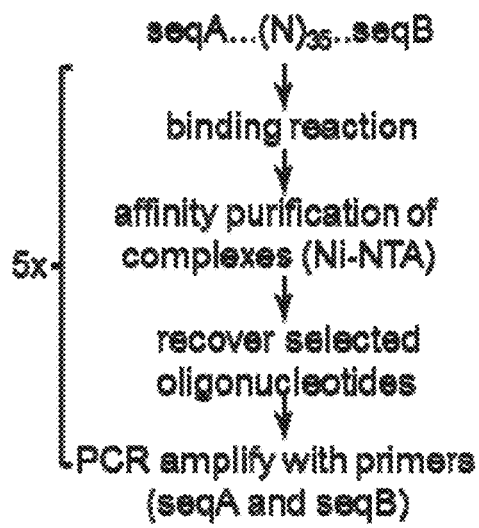
Figure 2B:
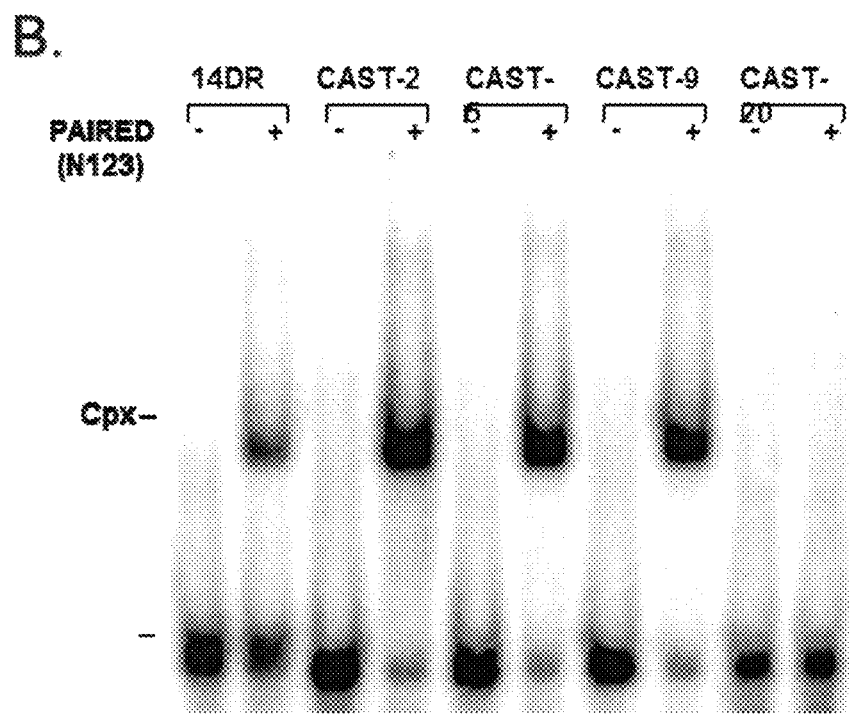
Figure 2C:
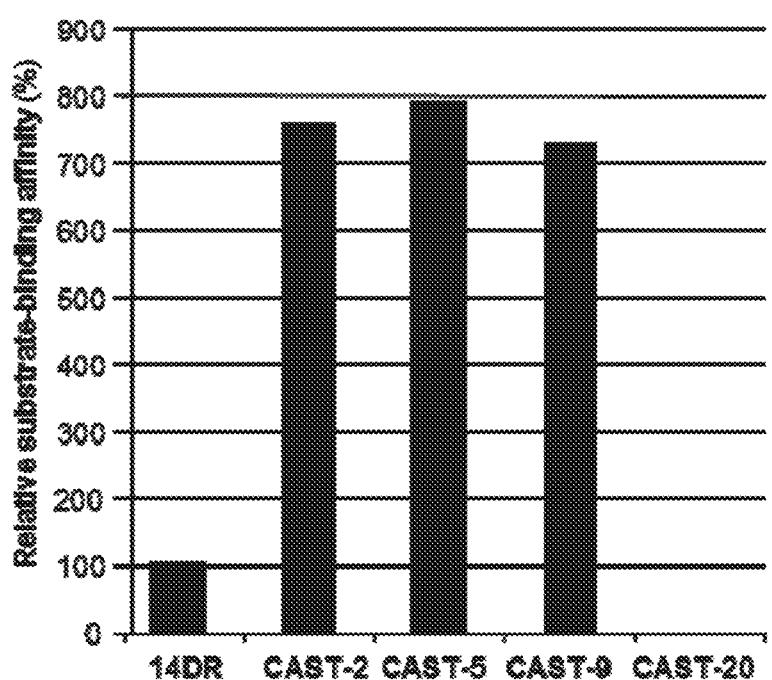
Figure 2D:
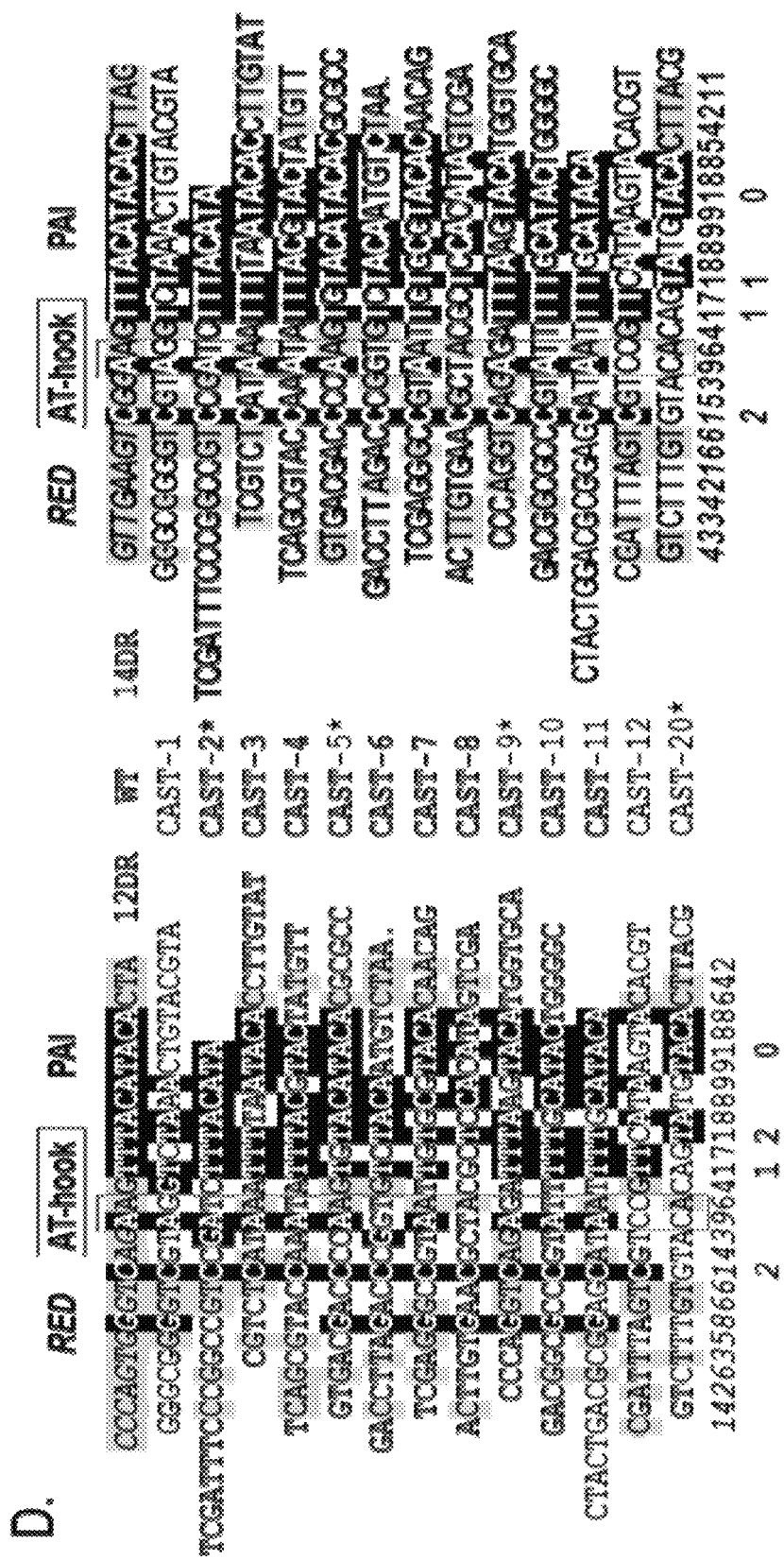

Although the binding site occupied by the PAIRED domain of SB has been determined (Ivics Z, et al., 1997. Cell, 91: 501-10), the footprinting experiment is not informative regarding the dynamic of substrate recognition. Are the binding motifs of PAI and RED recognised at the same time? To answer, the inventors have used the CASTing approach that was originally developed to identify optimal binding sites for DNA-binding proteins (Wright et al., 1991. Mol Cell Biol. 11:4104-10) (FIG. 2A). CASTing selects preferentially bound sequences out of complex libraries based on sequential enrichment of DNA sequences by affinity purification and PCR amplification. The CASTing approach as used to (i) identify high affinity binding sites, and (ii) map sequence motifs that are preferentially involved in primary substrate recognition by the composite DNA binding domain. Based on footprinting data of SB transposase binding (Ivics Z, et al., 1997. Cell, 91: 501-10), a 35-bp random oligonucleotide library was exposed to the full-length transposase upon binding conditions. Oligonucleotides selected after six CASTing cycles were sequenced and tested in electromobility shift assay (EMSA) using the full (PAIRED) DNA-binding domain of the transposase. The CASTing method selected sequences were bound up to eight-fold stronger when compared to the wild-type 14DR sequence (FIGS. 2B and 2C). Curiously, the CASTing-selected, high-affinity binding sites had only limited similarity to the wild-type DRs, and the identity concentrated mainly to the PAI recognition motif (FIG. 2D). Thus, while the PAI subdomain seems to specify primary substrate recognition (Izsvak Z, et al., 2002. J Biol Chem, 277: 34581-8; Carpentier C E, et al., 2014. Prot Sci. 23:23-33), RED is marginally involved in this process. The sequences captured by the CASTing strategy suggest that the PAI and RED DNA-interactions have distinct functions, and protein-DNA interaction by RED might take place at a later step, of the reaction. Furthermore, the CASTing-selected DRs are neither 12DR nor 14DR types, suggesting that there is no significant distinction between inner 12DR vs outer 14DR (FIG. 2D) during the 'first contact' between the transposon and transposase.

The RED Subdomain of the SB Transposase Mediates the Distinction Between 12DR vs 14DR The sequence recognized by either RED or PAI differs between 12 and 14DRs (FIG. 3A). Notably, RED binding overlaps with the two base pairs difference in length of 12 vs 14DRs (Izsvak Z, et al., 2002. Chem, 277: 34581-8.) (FIG. 3A), suggesting that RED might be involved in distinguishing between DRs located distantly (12DR) or proximally (14DR) to the end of the transposon. To test this assumption, double-stranded oligonucleotides representing the 12- and 14DRs were subjected to EMSA, using either the PAI (1-57 aa) or the RED (58-123 aa) subdomains of the SB transposase. As shown on FIG. 3B (lanes 3, 5 and 6), PAI equally bound to both DRs (FIG. 3B, lanes 2, 7, 8 and 13). In contrast, RED had a clear preference for 12DR (FIG. 3B, lanes 3, 5 and 6), and no significant binding was detected using the 14DR substrate (FIG. 3B, lane 12). Thus, RED can clearly distinguish between 12 vs 14DRs that might occur by recognizing sequence variation or difference in length. In order to distinguish between these possibilities, the EMSA was repeated with a 12DR-like oligonucleotide filled with 2 nucleotides having the same length as 14DR. Incorporation of two nucleotides into the 12DR abolished specific DNA binding (FIG. 3B, bottom, lanes 6 and 7) by RED, but left binding by PAI unaffected (FIG. 3B, bottom, lane 8). These results clearly indicated that RED distinguishes between inner and outer DRs by length and not sequence. The above data support the hypothesis that selective recognition of the inner (12DRs) vs outer (14DRs) transposase binding sites is guided by length difference between the 12- and 14DRs, recognized by the RED subdomain of the SB transposase. Curiously, RED does recognise 14DR located at the end of the inverted repeat in this experimental setup.

In Addition to 12/14DR Distinction, RED is Involved in Protein-Protein Interactions Although the PAI and RED subdomains are of similar size (57 and 66 amino acids, respectively), their nucleoprotein complexes migrate differently in EMSA (FIG. 3B). Based on mobility, PAI seems to bind both the 12- and 14DRs as a monomer. In contrast, using similar concentrations, the dominant nucleoprotein complex formed between RED and 12DR migrates slower, consistent with the complex containing two molecules of RED (FIG. 3B, lanes 3, 5 and 6). Notably, the complex formed by a RED monomer could be detected at a reduced protein concentration (20-fold less) in the binding reaction (FIG. 3B, lane 3). This observation suggests that RED readily forms dimers upon binding to the 12DR, suggesting that similarly to PAI, RED might be involved in both protein-DNA and protein-protein interactions. To test whether RED has a protein-protein interaction surface, the RED peptide was subjected to chemical cross-linking followed by Western blotting. Bands corresponding to dimeric, tetrameric and even higher order multimeric structures of RED were identified, both in the presence (FIG. 3C) or the absence of DNA substrate (not shown). These results indicate that similarly to PAI (Izsvak Z, et al., 2002. J Biol Chem, 277: 34581-8.), the RED subdomain is able to homodimerize. In sum, although both the PAI (Izsvak Z, et al., 2002. J Biol Chem, 277: 34581-8.) and RED subdomains have protein-protein interaction surfaces, only RED but not PAI forms dimers upon binding a single DNA substrate.

IR/DR Governs an 'Ordered Assembly' Process

Altering the affinity of the binding sites might challenge the ordered assembly process occurring during transposition of a SB transposon. Thus, a series of transposon versions were constructed where 12DR and/or 14DR motifs were replaced by CASTing selected, high affinity binding sites (FIG. 4A), and the various constructs were subjected to transposition assays. Surprisingly, replacing wild type motifs with the high-affinity CAST-5 sequence did not improve transposition frequencies. On the contrary, replacing either 12DRs or 14DRs to CAST-5 motif resulted in a 65% and 3% of wild type activities, respectively (FIG. 4A). Similarly, changing all the four DRs to CAST-5 affected transposition negatively (2.2%), suggesting that an enhanced DNA-binding affinity at either DR position might compromise SB transposition. Alternatively, the negative effect of CAST-5 on transposition could, at least partially, be accounted to its preferential selection for PAI binding, while compromising its RED function. Indeed, the CAST sequences are predicted to be sub-optimal for RED interaction, including the ability to distinguish between inner vs outer positions (FIG. 2). To distinguish between the two scenarios, we generated CAST-5/wt hybrids, where CAST-5 was replacing PAI only, otherwise kept the DRs wild type (wt). Again, we tested the impact of the hybrid motifs on transposition in various combinations. The high-affinity, CAST-5/wt hybrid motifs were still affecting transposition negatively at the outer and the combined inner/outer positions (FIG. 4B). However, the CAST-5/wt motif clearly improved transposition (130%), when replacing 12DRs at the inner positions (FIG. 4B).

The 'high affinity' experiments revealed the following features of SB transposition. First, although RED-14DR interaction could not be detected by EMSA, it was essential for transposition, assumingly at a later phase of the transposition reaction. Second, enhancing binding activity at the outer or at all the four DRs affects the transposition negatively, indicating that the DNA-binding affinity of the DRs at the inner vs outer positions cannot be freely changed. The substrate recognition seems to occur in well-defined steps at different phases of the reaction, directed by the IR/DR structure. During this process, PAI and RED subdomains are expected to perform multiple tasks involving DNA-protein and protein-protein interaction.

Finally, transposition could be improved by enhancing binding affinity of PAI at the inner positions (12DRs). Notably, the enhancement is not directly proportional with the optimised binding affinity, indicating that the IR/DR structure governs a delicately regulated process that does not tolerate drastic changes. Nevertheless, the attempt to decipher the role of the IR/DR structure in combination of molecular evolutionary approaches could be translated to significantly improve the transposition reaction of Sleeping Beauty.

Depletion of Components of the FACT Complex Increases Transposition Efficiency

A significant enrichment in transposition (involving SB10) was observed upon knockdown of SPT16 in stable knockdown HEK293T cells generated by RNA interference. (cf. FIG. 5, left column). Similarly, approximately, 50% enrichment was seen with SB100X (FIG. 5, right column. Knockdown of SUPT16H also led to increased transposition, while corresponding scrambled RNAi did not lead to any significant effect on transposition. Depletion of SUPT16H leads to the strongest effects.

A transposition assay in HEK293T cells that are transiently transfected with commercially available siRNAs for depletion of SPT16 or SUPT16H confirmed the results obtained using stable knockdown cell lines (FIG. 6).

Materials and Methods

Plasmid Constructs

Prokaryotic vectors pET-21a/N57, pET-21a/58-123 and pET-21a/N123 expressing hexahistidine-tagged subdomains of the SB DNA-binding domain, PAI, RED and N123 respectively, has been described previously (Izsvak Z, et al., 2002. J Biol Chem, 277: 34581-8.). For expression of the SB transposase in HeLa cells a pCMV-SB10 (Ivics et al., 1997, Cell 91:501-510). and pCMV-SBD3 (D3), a catalytic mutant (E278D) of SB, has been used. As donor plasmids in in vivo assays the following constructs have been used: pT/neo described previously (Ivics et al., 1997, Cell 91:501-510).

Protein Expression and Purification

Expression and purification of His-tagged PAI and RED subdomains were conducted as described in (Izsvak Z, et al., 2002. J Biol Chem, 277: 34581-8.).

Electromobility Shift Assay (EMSA)

Double-stranded oligonucleotides corresponding to either 12 or 14DRs were end-labeled using [$\alpha$-$^{32}$P]dCTP and Klenow fragment. The DNA probe containing the left IR was a EcoRI fragment of the pT/neo, end-labeled with [$\alpha$-$^{32}$P]dATP. Following the Klenow reaction, the labeled DNA was purified on MicroSpin G-25 Columns as described by the manufacturer. Binding reactions were performed in 20 mM HEPES (pH 7.5), 0.1 mM EDTA, 1 mM DTT in a total volume of 10 µl 20,000-50,000 cpm labeled DNA probe and various concentrations of the proteins (as noted in the Figures) were added and incubated 10 min on ice. After addition of 3 µl of loading dye (containing 50% glycerol and bromophenol blue) the samples were loaded onto a 4% or 6% polyacrylamide gel. The electrophoresis was carried out in Tris-glycine buffer pH 8.3 at 25 mA for 2-3 hours. The gels were dried for 45 minutes using the gel dryer from BIO-RAD. After overnight exposure the gels were scanned with Fujifilm FLA-3000 and analysed with AIDA program.

Sequence of probes used in the experiments:
14DR:
S
(SEQ ID NO: 79)
5'-ACATACACTTAAGTGTATGTAAACTTCCGACTTCAACTTGG-3'

AS
(SEQ ID NO: 80)
5'-GACTCCAAGTTGAAGTCGGAAGTTTACATACACTTAAGTGTATGT-3'

-continued

12DR:
S
(SEQ ID NO: 81)
5'-ACATACATTAGTGTATGTAAACTTCTGACCCACTGTTGG-3'

AS
(SEQ ID NO: 82)
5'-GACTCCAACAGTGGGTCAGAAGTTTACATACACTAATGTATGT-3'

CAST-2
S
(SEQ ID NO: 34)
5'-acatacaccctggtgtatgtaaagatcggacggccggttgg-3'

AS
(SEQ ID NO: 35)
5'-gactccaaccggccgtccgatattacatacaccagggtgtatgt-3'

CAST-5
S
(SEQ ID NO: 36)
5'-acatacaggcgcgtgtatgtacacttggggtcgtcacttgg-3'

AS
(SEQ ID NO: 37)
5'-gactccaagtgacgacccaagtgtacatacacgcgcctgtatgt-3'

CAST-9
S
(SEQ ID NO: 38)
5'-acatacagcaccatgtacttaaatctctgacctgggcttgg-3'

AS
(SEQ ID NO: 39)
5'-gactccaagcccaggtcagagatttaagtacatggtgctgtatgt-3'

CAST-20
S
(SEQ ID NO: 40)
5'-acatacacgtaagtgtacatactgtgtacacaaagacttgg-3'

AS
(SEQ ID NO: 41)
5'-gactccaagtctttgtgtacacagtatgtacacttacgtgtatgt-3'

Chemical Crosslinking

Reactions were performed using the bis(sulfosuccinimidyl) substrate (BS³, Pierce Biotechnology, USA) according to manufacturer's recommendations. Proteins (3 μM) were incubated on ice in 20 mM HEPES (pH 7.5), 5 mM MgCl₂, 100 mM NaCl and 2.5 mM BS³ in a final volume of 15 μl for 2 hours. The reactions were stopped by adding Tris-HCl pH 7.5 to a final concentration of 50 mM and incubating 10 min at room temperature. Then the Laemli buffer (125 mM Tris-HCI pH 6.8, 5% SDS, 10% β-mercaptoethanol, 25% glycerol and bromophenol blue) was added and samples were loaded on 15% SDS-PAGE and analyzed by Western blotting using polyclonal anti-SB antibody (R&D Systems, USA) and anti-goat IgG (Pierce Biotechnology, USA).

CASTing Experiment

The CASTing was performed based on the method described in Wright, Binder et al. (1991). Oligonucleotides with random 35 bp long core SB-DOL: 5'-GCG GGA TCC ACT CCA GGC CGG ATG CT (N)₃₅ CAC CAG GGT GTA AGG CGG ATC CCG C -3' (SEQ ID NO: 42) were synthesized and made double-stranded in a PCR reaction with primers complementary to the sequences flanking the core. The nucleoprotein complexes formed during 1 h incubation of 2 μg of the oligonucleotides with 0.15 μg of the purified His-tagged SB transposase (SBFT-6H) (Izsvak Z, et al., 2002. J Biol Chem, 277: 34581-8.) were recovered using the Ni-NTA resin (QIAGEN). The bound oligonucleotides were enriched by extensive washing steps. The selected oligonucleotides were extracted and amplified by primers A, 5'-GCG GGA TCC GCC TTA CAC CCT GGT G -3' (SEQ ID NO: 43) and B, 5'-GCG GGA TCC ACT CCA GGC CGG ATG CT -3' (SEQ ID NO: 44), and subjected to additional rounds of the CASTing cycle to increase the specificity of the method. The oligonucleotides obtained from 6$^{th}$ round were sequenced and tested in binding and transposition assays.

Cell Culture

HeLa cells were grown in DMEM (GIBCO BRL, Germany) supplemented with 10% Fecal Calf Serum Gold (FCS Gold) (PAA, Germany) and 1% antimycotic antibiotic (Invitrogen, Germany). One day prior transfection cells were seeded onto six-well plates. Cells were transfected with Qiagen purified DNA (Qiaprep spin miniprep kit, Qiagen) using jetPEI RGD transfection reagent (Polyplus Transfection, France). Two days posttransfection cells were harvested for excision assay and/or were plated out on 10 cm plates for selection using 1 mg/ml G418 (Biochrom, Germany). After 3 weeks of selection, colonies were stained and counted as described in Ivics et al., Cell 1997.

Sleeping Beauty Transposon Excision Assay

In order to determine the excision efficiency during sleeping beauty transposon transposition from plasmids to genome, we cloned a Sleeping Beauty transposon-based reporter called pCMV(CAT)-GFP/T2neo. In detail, firstly, the open reading frame of GFP controlled by the CMV promoter was cloned into the pcDNA3.1 vector. Then, the sleeping beauty transposon containing a selection gene neo (driven by the SV40 promoter) was cloned into the 'TA' site in GFP ORF.

To evaluate the effects of internal sequence of the sleeping beauty transposon on excision efficiency, 977-bp and 1654-bp sequences (containing partial SV40-neo) were cut out from the original excision reporter, respectively, to clone two alternative excision reporters with shorter internal sequences (1260 bp and 583 bp respectively).

The three transposon constructs were purified using the Qiagen plasmid midi kit. The purified plasmid DNA was transfected into HeLa cells with the transposase-expressing plasmid pCMV(CAT)SB100X (Mátés L, et al. Molecular evolution of a novel hyperactive Sleeping Beauty transposase enables robust stable gene transfer in vertebrates. Nat Genet. 2009 June; 41(6):753-61.) using jetPEI (Polyplus transfection, for mammalian cells) according to instructions of manufacture. Three days later, the number of GFP-positive cells was estimated by FACS.

Cloning

Mutated SB transposon ends were created by PCR-mediated mutagenesis. Primer sequences and cloning strategies are summarized in Table 1.

TABLE 4

| | SEQ ID NO: | Primer sequences | Template of the PCR | Cloning strategy |
|---|---|---|---|---|
| Construct 2 | 57 | 5'-tacagtgacgacccaagtgtacatacacgcgccccaaatacat-3' | pT/neo | Ligate to SmaI site of pUC19 |
| | 58 | 5'-tacagtgacgacccaagtgtacatacacgcgccttggagtcatta-3' | | |

TABLE 4-continued

| | SEQ ID NO: | Primer sequences | Template of the PCR | Cloning strategy |
|---|---|---|---|---|
| Construct 3 | 59 | 5'-gtacatacacgcgcttagtatttggtagcattgccttta-3' | pT/neo | Ligate the 2 fragments |
| | 60 | 5'-gtacatacacgcgcttgactgtgcctttaaacagcttgg-3' | | |
| | 61 | 5'-acttggggtcgtcaccaattgtgatacagtgaattataagtg-3' | pT/neo | |
| | 62 | 5'-acttggggtcgtcaccgaatgtgatgaaagaaataaaagc-3' | | |
| Construct 4 | 63 | 5'-gtacatacacgcgcttagtatttggtagcattgccttta-3' | pT/neo | Ligate the 2 fragments |
| | 64 | 5'-gtacatacacgcgcttgactgtgcctttaaacagcttgg-3' | | |
| | 65 | 5'-acttggggtcgtcaccaattgtgatacagtgaattataagtg-3' | Construct2 | |
| | 66 | 5'-acttggggtcgtcaccgaatgtgatgaaagaaataaaagc-3' | | |
| Construct 5 | 67 | 5'-acttccgacttcaactgtaggggatcctctagagtcgacctg-3' | pT/neo | Ligate the 2 fragments |
| | 68 | 5'-acttccgacttcaactgtagggtaccgagctcgaattcactg-3' | | |
| | 69 | 5'-gtacatacacgcgccccaaatacatttaaactcactttttc-3' | pT/neo | |
| | 70 | 5'-gtacatacacgcgccttggagtcattaaaactcgtttttc-3' | | |
| Construct 6 | 71 | 5'-acttctgacccactgggaatgtgatgaaagaaataaaagc-3' | pT/neo | Ligate the 2 fragments |
| | 72 | 5'-acttctgacccactggaattgtgatacagtgaattataagtg-3' | | |
| | 73 | 5'-gtacatacacgcgcttagtatttggtagcattgccttta-3' | pT/neo | |
| | 74 | 5'-gtacatacacgcgcttgactgtgcctttaaacagcttgg-3' | | |
| Construct 7 | 75 | 5'-gtacatacacgcgcttagtatttggtagcattgccttta-3' | pT/neo | Ligate the 2 fragments |
| | 76 | 5'-gtacatacacgcgcttgactgtgcctttaaacagcttgg-3' | | |
| | 77 | 5'-acttctgacccactgggaatgtgatgaaagaaataaaagc-3' | Construct5 | |
| | 78 | 5'-acttctgacccactggaattgtgatacagtgaattataagtg-3' | | |

Depletion of Components of the FACT Complex Increases Transposition Efficiency miRNA constructs were generated using the target microRNAs described in Table 5. For establishing stable knockdown cell lines, Hek293T cells were transduced with said micro RNA constructs.

microRNA (miRNA) based vector was used for stable knockdown cell clines of ssrp1 and supt16H, comprising the components MPSV-LTR—Intron—truncated hNGFR—WPRE—miRNA—LTR Myeloproliferative sarcoma virus (MPSV); Long terminal repeat (LTR) of mouse; Truncated human nerve growth factor receptor (NGFR); Woodchuck hepatitis virus (WHP) posttranscriptional regulatory element (wPRE); Core sequence of mouse miR155 with target (ssrp1 or supt16H) sense and antisense sequences.

The expression of the micro RNA was monitored by staining the cells with anti-NGFR antibody. For enriching the cell population with micro RNAs, cells were FACS sorted and cultured. For analysing the knockdown efficiency, enriched cell population was subjected for RNA isolation followed by cDNA synthesis. The expression level of the target genes was monitored by qPCR with gene specific primes (as listed in Table 6).

Pre-designed, commercial, synthetic, siRNAs (siGENOME, SMARTpool) were procured (from Dharmacon, GE healthcare). siRNAs targeting either supt16H gene (cat. No. M-009517-00-0005) and ssrp1 (cat. No. M-011783-01-0005) were transfected into Hek293T using jetPEI™ transfection system. As a negative control siRNA targeting firefly luciferase gene (cat. No. D-001206-14-05) was used. 24 h later, cells were transfected with respective plasmids for transposition. Two days post transfection; the transfected cells were trypsinized, counted and subjected for puromycin selection. After one week of selection, colonies were fixed with 10% formaldehyde in PBS for 15 min, stained with methylene blue in PBS for 30 min, washed extensively with deionized water, air dried, and photographed.

A transposition assay was performed as published previously (Ivics Z, et al., 1997. Cell, 91: 501-10), Results are shown in FIGS. 5 and 6.

TABLE 5 miRNA sequences for knockdown

| Name | Sequence | Application |
|---|---|---|
| Scramble | (as) 5' <u>TAG GTC CTC TTC ATC TTG TTG</u> 3' (SEQ ID NO: 83)<br>(ss) 3' ATC CAC GAG AAG TAG AAC AAC 5' (SEQ ID NO: 84) | miRNA not targeting any gene |
| ssrp1 | (as) 5' <u>TTT ACC AGT GCT TTC ATG AGG</u> 3' (SEQ ID NO: 85)<br>(ss) 3' AAA TGG TCA CGA AAG TAC TGG 5' (SEQ ID NO: 86) | miRNA targeting ssrp1 gene |

TABLE 5-continued miRNA sequences for knockdown

| Name | Sequence | Application |
|---|---|---|
| supt16H | (as) 5' ATC AAA GTG CGA ACA AGG TTG 3' (SEQ ID NO: 87)<br>(ss) 3' TAG TTT CAC GCT TGT TCC AAC 5' (SEQ ID NO: 88) | miRNA targeting supt16H gene |

TABLE 6

Primers

| Name | Primer | Sequence | Application |
|---|---|---|---|
| Supt16H | Forward primer | 5' CATTGGTGACACAGTGCTTGTGG 3' (SEQ ID NO: 89) | qPCR |
| | Reverse primer | 5' CCAAAAGGTCCTCTGCCTCATC 3' (SEQ ID NO: 90) | |
| Ssrp1 | Forward primer | 5' TCACAGTGCCAGGCAACTTCCA 3' (SEQ ID NO: 91) | qPCR |
| | Reverse primer | 5' ACAGGTGGCTTGTGGACGTAGA 3' (SEQ ID NO: 92) | |

Example 2

It has been previously shown that both DNA-PKcs and ATM activities are required for efficient SB transposition (Izsvák et al., 2004, Mol Cell 13(2):279-90). Similarly to DNA-PKcs and ATM, ATR also belongs to the phosphatidylinositol 3 kinase-like kinase (PIKK) family, involved in checkpoint signalling and repair. ATR specifically gets activated by DNA damage during replication (Lupardus et al., 2002, Genes Dev 16(18):2327-32). Caffeine is an inhibitor of ATM, ATR and mTOR (also a PIKK member), but not of DNA-PKCs (Sarkaria et al., 1999, Cancer Res. 59(17):4375-82). The inventors examined SB transposition using a standard transposition assay, under caffeine treatment (4 mM).

Figure 7B:
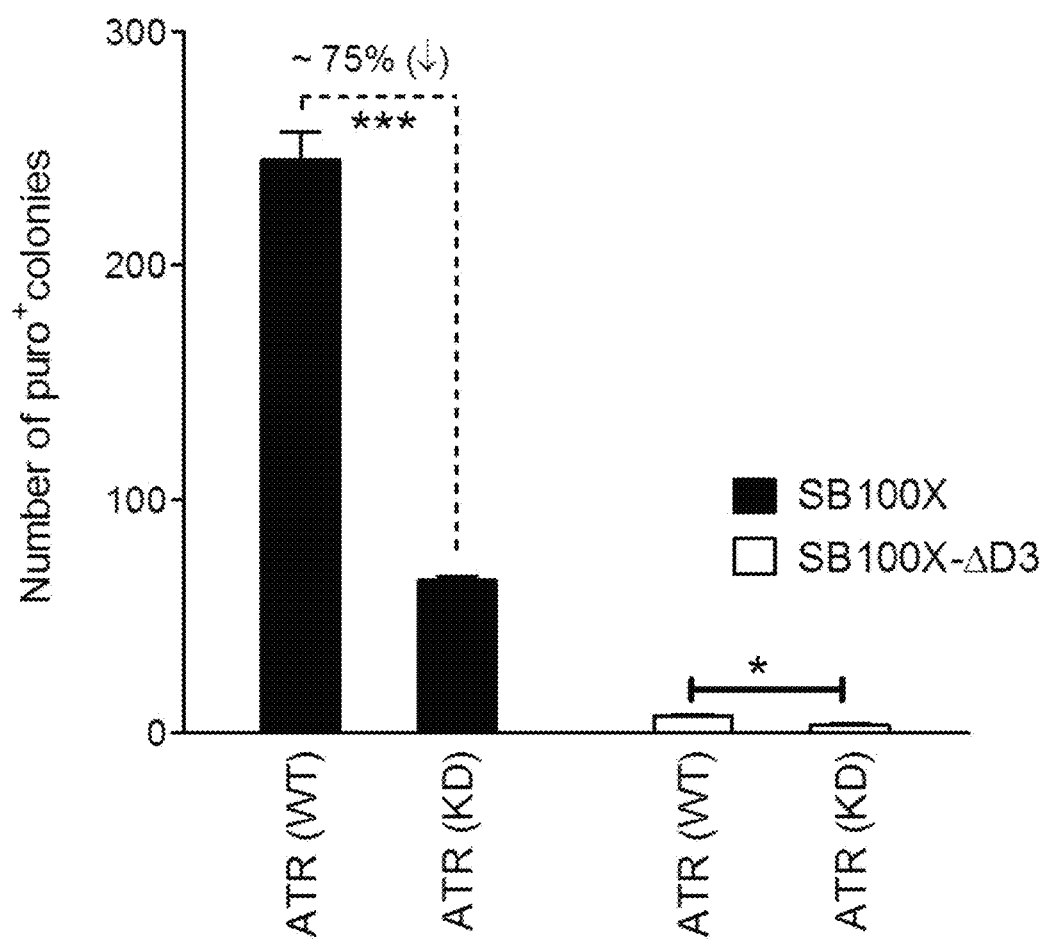

The frequency of transposition was decreased by approximately 50% upon caffeine treatment relative to the control (FIG. 7A). In order to decipher if ATR signalling is specifically required for efficient SB transposition, stable TET-inducible cell lines, where ATR function can be regulated were used. SB transposition was monitored in stable cell lines expressing either ATR (wildtype) or ATRkd (a dominant negative kinase-inactive allele of ATR) in an inducible manner (Cliby et al., 1998, EMBO J. 17(1):159-69). Expression of ATRkd, a catalytically dead version of ATR has as a dominant negative effect that disables ATR activity (Cliby et al., 1998). In ATR-disabled cells, ATR is not able to initiate the signalling cascade that would resolve replication arrest. ATR and ATRkd were induced, and the two lines were subjected to the genomic transposition assay. The results show that transposition dropped by ~75% in ATR disabled cells, indicating that ATR is essential for SB transposition (FIG. 7B). Furthermore, in spite of stalled replication forks accumulation in ATRkd induced cells, induction of transposition was not observed, suggesting that intact ATR signalling may be required for triggering transposition.

The invention claimed is:

1. A polynucleotide or the complementary polynucleotide thereof comprising a transposon comprising a cargo nucleic acid flanked by a left and a right inverted repeat/direct repeat (IR/DR), wherein
   (i) the transposon is capable of being mobilized by a Sleeping Beauty transposase protein;
   (ii) the left IR/DR comprises an outer left DR motif and an inner left DR motif, wherein the outer left DR motif comprises the nucleotide sequence of SEQ ID NO:1 and the inner left DR motif comprises the nucleotide sequence of SEQ ID NO: 2; and
   (iii) the right IR/DR comprises an outer right DR motif and an inner right DR motif, wherein the outer right DR motif comprises a reverse complement of the nucleotide sequence of SEQ ID NO:1 and the inner right DR motif comprises a reverse complement of the nucleotide sequence of SEQ ID NO: 2.

2. The polynucleotide of claim 1, wherein the outer left DR motif comprises the nucleotide sequence of SEQ ID NO: 3 and/or the outer right DR motif comprises a reverse complement of the nucleotide sequence of SEQ ID NO: 4.

3. The polynucleotide of claim 1, wherein the inner left DR motif comprises the nucleotide sequence of SEQ ID NO: 5 and/or the inner right DR motif comprises a reverse complement of the nucleotide sequence of SEQ ID NO: 6.

4. The polynucleotide of claim 1, wherein the left IR/DR comprises a half direct repeat (HDR) region capable of functioning as an enhancer comprising the nucleotide sequence of SEQ ID NO:7 between the outer DR and inner DR, wherein, optionally, the right IR/DR also comprises reverse complement of said HDR region.

5. The polynucleotide of claim 1, wherein the left IR/DR comprises the nucleotide sequence selected from the group consisting of SEQ ID NO: 8 and SEQ ID NO:9.

6. The polynucleotide of claim 1, wherein the right IR/DR comprises the reverse complement nucleotide sequence selected from the group consisting of SEQ ID NO: 10, SEQ ID NO:11, SEQ ID NO: 12 and SEQ ID NO: 13.

7. The polynucleotide of claim 1, wherein the cargo nucleic acid comprises an open reading frame operably linked to a promotor.

8. The polynucleotide of claim 7, wherein the open reading frame encodes a T-cell receptor construct.

9. An isolated cell comprising the polynucleotide of claim 7, wherein the isolated cell is a T-cell capable of adoptive T-cell transfer.

10. A pharmaceutical composition comprising the isolated cell of claim 9.

11. The polynucleotide of claim 1, wherein the Sleeping Beauty transposase is hyperactive transposase SB100X.

12. The polynucleotide of claim 1, wherein the polynucleotide is a vector selected from the group consisting of
   (i) a viral vector selected from the group comprising an adenoviral, adeno-associated viral, lentiviral, retroviral, herpes simplex viral, baculovirus, Epstein-Barr viral, and poxvirus vector; and
   (ii) a non-viral vector selected from the group comprising a plasmid, a minicircle, a pFAR vector or a virosome.

13. An isolated cell comprising the polynucleotide of claim 1.

14. A pharmaceutical composition comprising the isolated cell of claim 13.

15. A kit for transposing a nucleic acid, wherein the kit comprises
   (i) the polynucleotide of claim 1;
   (ii) (a) a Sleeping Beauty transposase protein or (b) a nucleic acid encoding a Sleeping Beauty transposase protein.

16. The kit of claim 15, wherein the Sleeping Beauty transposase is hyperactive transposase SB100X.

17. The kit of claim 15, further comprising
   (iii) at least one cofactor selected from the group consisting of
     (A) a cofactor capable of depleting a component of the FACT complex selected from the group consisting of SSRP1 and SUPT16H/SPT16;
     (B) an inhibitor of cathepsin selected from the group comprising H, S, V, and L;
     (C) a cofactor capable of depleting or inhibiting HSP90;
     (D) a factor temporally arresting cells cell cycle in cell cycle phase G0/G1, G1/S, or G2/M;

(E) a factor inhibiting the ubiquitination of PCNA, and
(F) an agent capable of increasing concentration and/or signaling of ATR,
wherein said cofactor is selected from the group comprising a small molecule, siRNA and miRNA.

18. The kit of claim 15, further comprising
(iii) a cell wherein one or more components comprising:
(AA) a component of the FACT complex selected from the group consisting of SSRP1 and SUPT16H/SPT16 is knocked down; or
(BB) cathepsin is knocked down; or
(CC) HSP90, is knocked down; or
(DD) the cell cycle is temporally arrested in cell cycle phase G0/G1, G1/S, or G2/M; or
(EE) the ubiquitination of PCNA is inhibited; or
(FF) concentration or signaling of ATR is increased.

19. A method of producing a recombinant nucleic acid, comprising contacting a target nucleic acid comprising a recognition sequence for a Sleeping Beauty transposase with the components of the kit of claim 15; wherein the recombinant nucleic acid is produced by integration of the transposon into the target nucleic acid.

20. The method of claim 19, wherein the Sleeping Beauty transposase is hyperactive transposase SB100X.

21. A method of producing a transfected cell, wherein the method comprises introducing into a cell the components of the kit of claim 15, thereby producing said transfected cell.

22. The method of claim 21, wherein the Sleeping Beauty transposase is hyperactive transposase SB100X.

23. A method for preparing a recombinant polynucleotide or a recombinant cell comprising a recombinant polynucleotide by transposition of a transposon, wherein the transposon is the polynucleotide of claim 1, comprising introducing a cofactor selected from the group consisting of
(A) a cofactor capable of depleting a component of the facilitates chromatin transcription (FACT) complex selected from the group consisting of SSRP1 and SUPT16H/SPT16;
(B) an inhibitor of cathepsin selected from the group comprising H, S, V, and L;
(C) a cofactor capable of depleting or inhibiting HSP90;
(D) a factor temporally arresting cells cell cycle in cell cycle phase G0/G1, G1/S, or G2/M;
(E) a factor inhibiting the ubiquitination of a Proliferating Cell Nuclear Antigen (PCNA); and
(F) an agent capable of increasing concentration and/or signaling of ataxia telangiectasia and Rad3 related (ATR),
wherein the cofactor is selected from the group comprising a small molecule, an antibody, siRNA and miRNA,
or comprising inducing transposition in a cell or a cell wherein one or more of:
(AA) said component of the FACT complex; or
(BB) said cathepsin; or
(CC) said HSP90 is knocked down; or
(DD) the cell cycle is temporally arrested in cell cycle phase G0/G1, G1/S, or G2/M; or
(EE) the ubiquitination of PCNA is inhibited; or
(FF) concentration or signaling of ATR is increased.

* * * * *

UNITED STATES PATENT AND TRADEMARK OFFICE
CERTIFICATE OF CORRECTION

PATENT NO. : 11,814,643 B2
APPLICATION NO. : 16/085012
DATED : November 14, 2023
INVENTOR(S) : Zsuzsanna Izsvák et al.

Page 1 of 1

It is certified that error appears in the above-identified patent and that said Letters Patent is hereby corrected as shown below:

On the Title Page

In item (73) Assignee, "Max-Delbrück-Centrum für Molekulage Medizin in der Helmholtz-Gemeinschaft." should read -- Max-Delbrück-Centrum für Molekulare Medizin in der Helmholtz-Gemeinschaft --

In the Specification

In Column 2, Lines 54-55, "Different variants of SB transposons are known in the art 8,227,432, Cui et al., 2002." should read -- Different variants of SB transposons are known in the art (WO 98/40510, US 8,227,432, Cui et al., 2002. --

Signed and Sealed this
Twenty-seventh Day of February, 2024

Katherine Kelly Vidal
*Director of the United States Patent and Trademark Office*

SEQUENCE LISTING

<160> NUMBER OF SEQ ID NOS: 92

<210> SEQ ID NO 1
<211> LENGTH: 32
<212> TYPE: DNA
<213> ORGANISM: Artificial Sequence
<220> FEATURE:
<223> OTHER INFORMATION: pT 4/5 consensus sequence outer DR

<400> SEQUENCE: 1
cagttgaagt cggaagttta catacacytw ag                                32

<210> SEQ ID NO 2
<211> LENGTH: 32
<212> TYPE: DNA
<213> ORGANISM: Artificial Sequence
<220> FEATURE:
<223> OTHER INFORMATION: pT4/5 consensus sequence inner DR

<400> SEQUENCE: 2

```
yccagtgggt cagaagtgta catacacgvk ct                              32
```

<210> SEQ ID NO 3
<211> LENGTH: 32
<212> TYPE: DNA
<213> ORGANISM: Artificial Sequence
<220> FEATURE:
<223> OTHER INFORMATION: pT4/5 left outer DR

<400> SEQUENCE: 3

```
cagttgaagt cggaagttta catacactta ag                              32
```

<210> SEQ ID NO 4
<211> LENGTH: 32
<212> TYPE: DNA
<213> ORGANISM: Artificial Sequence
<220> FEATURE:
<223> OTHER INFORMATION: pT4/5 right outer DR

<400> SEQUENCE: 4

```
cagttgaagt cggaagttta catacacctt ag                              32
```

<210> SEQ ID NO 5
<211> LENGTH: 32
<212> TYPE: DNA
<213> ORGANISM: Artificial Sequence
<220> FEATURE:
<223> OTHER INFORMATION: pT4/5 left inner DR

<400> SEQUENCE: 5

```
tccagtgggt cagaagtgta catacacgvk ct                              32
```

<210> SEQ ID NO 6
<211> LENGTH: 32
<212> TYPE: DNA
<213> ORGANISM: Artificial Sequence
<220> FEATURE:
<223> OTHER INFORMATION: pT4/5 right inner DR

<400> SEQUENCE: 6

```
cccagtgggt cagaagtgta catacacgvk ct                              32
```

<210> SEQ ID NO 7
<211> LENGTH: 13
<212> TYPE: DNA
<213> ORGANISM: Artificial Sequence
<220> FEATURE:
<223> OTHER INFORMATION: HDR

<400> SEQUENCE: 7

```
gtktacakac asd                                                   13
```

<210> SEQ ID NO 8
<211> LENGTH: 231
<212> TYPE: DNA
<213> ORGANISM: Artificial Sequence
<220> FEATURE:
<223> OTHER INFORMATION: Left IR/DR of pT4 with HDR

<400> SEQUENCE: 8

```
tacagttgaa gtcggaagtt tacatacacy twagttggag tcattaaaac tcgttttca    60 actactccac aaatttcttg ttaacaaaca atagttttgg caagtcagtt aggacatcta   120
ctttgtgcat gacacaagtc attttccaa caattgtkta cakacasdtt atttcactta   180
```

```
taattcactg tatcacaaty ccagtgggtc agaagtgtac atacacgvkc t            231
```

<210> SEQ ID NO 9
<211> LENGTH: 233
<212> TYPE: DNA
<213> ORGANISM: Artificial Sequence
<220> FEATURE:
<223> OTHER INFORMATION: Left IR/DR of pT5 with HDR

<400> SEQUENCE: 9

```
tatacagttg aagtcggaag tttacataca cytwagttgg agtcattaaa actcgttttt    60
caactactcc acaaatttct tgttaacaaa caatagtttt ggcaagtcag ttaggacatc   120
tactttgtgc atgacacaag tcattttcc aacaattgtk tacakacasd ttatttcact    180
tataattcac tgtatcacaa tyccagtggg tcagaagtgt acatacacgv kct          233
```

<210> SEQ ID NO 10
<211> LENGTH: 232
<212> TYPE: DNA
<213> ORGANISM: Artificial Sequence
<220> FEATURE:
<223> OTHER INFORMATION: Right IR/DR of pT4 without HDR (right IR/DR
      comprises the reverse complement of the given sequences)

<400> SEQUENCE: 10

```
tacagttgaa gtcggaagtt tacatacacy twagccaaat acatttaaac tcactttttc    60
acaattcctg acatttaatc cgagtaaaga ttccctgtct taaggtcagt taggatcacc   120
actttatttt aagaatgtga aatatcagaa taatagtaga gagaatgatt catttcagct   180
tttatttctt tcatcacatt yccagtgggt cagaagtgta catacacgvk ct           232
```

<210> SEQ ID NO 11
<211> LENGTH: 233
<212> TYPE: DNA
<213> ORGANISM: Artificial Sequence
<220> FEATURE:
<223> OTHER INFORMATION: Right IR/DR of pT5 without HDR (right IR/DR
      comprises the reverse complement of the given sequences):

<400> SEQUENCE: 11

```
tatacagttg aagtcggaag tttacataca cytwagccaa atacatttaa actcactttt    60
tcacaattcc tgacatttaa tcctagtaaa aattccctgt cttaggtcag ttaggatcac   120
cactttattt taagaatgtg aaatatcaga ataatagtag agagaatgat tcatttcagc   180
ttttatttct tcatcacat tyccagtggg tcagaagtgt acatacacgv kct           233
```

<210> SEQ ID NO 12
<211> LENGTH: 245
<212> TYPE: DNA
<213> ORGANISM: Artificial Sequence
<220> FEATURE:
<223> OTHER INFORMATION: Right IR/DR of pT4 with HDR (right IR/DR
      comprises the reverse complement of the given sequences)

<400> SEQUENCE: 12

```
tacagttgaa gtcggaagtt tacatacacy twagccaaat acatttaaac tcactttttc    60
acaattcctg acatttaatc cgagtaaaga ttccctgtct taaggtcagt taggatcacc   120
actttatttt aagaatgtga aatatcagaa taatagtaga gagaatgatg tktacakaca   180
sdtcatttca gcttttattt ctttcatcac attyccagtg ggtcagaagt gtacatacac   240 gvkct                                                               245
```

```
<210> SEQ ID NO 13
<211> LENGTH: 246
<212> TYPE: DNA
<213> ORGANISM: Artificial Sequence
<220> FEATURE:
<223> OTHER INFORMATION: Right IR/DR of pT5 with HDR (right IR/DR
      comprises the reverse complement of the given sequences)

<400> SEQUENCE: 13
tatacagttg aagtcggaag tttacataca cytwagccaa atacatttaa actcactttt      60
tcacaattcc tgacatttaa tcctagtaaa aattccctgt cttaggtcag ttaggatcac     120
cactttattt taagaatgtg aaatatcaga ataatagtag agagaatgat gtktacakac     180
asdtcatttc agcttttatt tctttcatca cattyccagt gggtcagaag tgtacataca     240 cgvkct                                                                246

<210> SEQ ID NO 14
<211> LENGTH: 29
<212> TYPE: DNA
<213> ORGANISM: Artificial Sequence
<220> FEATURE:
<223> OTHER INFORMATION: 12DR WT

<400> SEQUENCE: 14
cccagtgggt cagaagttta catacacta                                        29

<210> SEQ ID NO 15
<211> LENGTH: 29
<212> TYPE: DNA
<213> ORGANISM: Artificial Sequence
<220> FEATURE:
<223> OTHER INFORMATION: 14DR WT

<400> SEQUENCE: 15
gttgaagtcg gaagtttaca tacacttag                                        29

<210> SEQ ID NO 16
<211> LENGTH: 30
<212> TYPE: DNA
<213> ORGANISM: Artificial Sequence
<220> FEATURE:
<223> OTHER INFORMATION: 12DR CAST-1

<400> SEQUENCE: 16
gggcggggtc gtaggtctaa actgtacgta                                       30

<210> SEQ ID NO 17
<211> LENGTH: 30
<212> TYPE: DNA
<213> ORGANISM: Artificial Sequence
<220> FEATURE:
<223> OTHER INFORMATION: 14DR CAST-1

<400> SEQUENCE: 17
gggcggggtc gtaggtctaa actgtacgta                                       30

<210> SEQ ID NO 18
<211> LENGTH: 30
<212> TYPE: DNA
<213> ORGANISM: Artificial Sequence
<220> FEATURE:
<223> OTHER INFORMATION: 12DR CAST-2

<400> SEQUENCE: 18
```
tcgatttccc ggccgtccga tctttacata        30

<210> SEQ ID NO 19
<211> LENGTH: 30
<212> TYPE: DNA
<213> ORGANISM: Artificial Sequence
<220> FEATURE:
<223> OTHER INFORMATION: 14DR CAST-2

<400> SEQUENCE: 19
tcgatttccc ggccgtccga tctttacata        30

<210> SEQ ID NO 20
<211> LENGTH: 29
<212> TYPE: DNA
<213> ORGANISM: Artificial Sequence
<220> FEATURE:
<223> OTHER INFORMATION: 12DR CAST-3

<400> SEQUENCE: 20
cgtctcataa attttaatac accttgtat        29

<210> SEQ ID NO 21
<211> LENGTH: 31
<212> TYPE: DNA
<213> ORGANISM: Artificial Sequence
<220> FEATURE:
<223> OTHER INFORMATION: 14DR CAST-3

<400> SEQUENCE: 21
tcgtctcata aattttaata caccttgtat c        31

<210> SEQ ID NO 22
<211> LENGTH: 30
<212> TYPE: DNA
<213> ORGANISM: Artificial Sequence
<220> FEATURE:
<223> OTHER INFORMATION: 12DR CAST-4

<400> SEQUENCE: 22
tcagcgtacc aaatatttac gtactatgtt        30

<210> SEQ ID NO 23
<211> LENGTH: 30
<212> TYPE: DNA
<213> ORGANISM: Artificial Sequence
<220> FEATURE:
<223> OTHER INFORMATION: 14DR CAST-4

<400> SEQUENCE: 23
tcagcgtacc aaatatttac gtactatgtt        30

<210> SEQ ID NO 24
<211> LENGTH: 30
<212> TYPE: DNA
<213> ORGANISM: Artificial Sequence
<220> FEATURE:
<223> OTHER INFORMATION: 12DR CAST-5

<400> SEQUENCE: 24
gtgacgaccc caagtgtaca tacacgcgcc        30

<210> SEQ ID NO 25
<211> LENGTH: 30
<212> TYPE: DNA
<213> ORGANISM: Artificial Sequence

<220> FEATURE:
<223> OTHER INFORMATION: 14DR CAST-5

<400> SEQUENCE: 25
gtgacgaccc caagtgtaca tacacgcgcc                                    30

<210> SEQ ID NO 26
<211> LENGTH: 30
<212> TYPE: DNA
<213> ORGANISM: Artificial Sequence
<220> FEATURE:
<223> OTHER INFORMATION: 12DR CAST-6

<400> SEQUENCE: 26
gaccttagac ccggtgtcta caatgtctaa                                    30

<210> SEQ ID NO 27
<211> LENGTH: 30
<212> TYPE: DNA
<213> ORGANISM: Artificial Sequence
<220> FEATURE:
<223> OTHER INFORMATION: 14DR CAST-6

<400> SEQUENCE: 27
gaccttagac ccggtgtcta caatgtctaa                                    30

<210> SEQ ID NO 28
<211> LENGTH: 30
<212> TYPE: DNA
<213> ORGANISM: Artificial Sequence
<220> FEATURE:
<223> OTHER INFORMATION: 12DR CAST-7

<400> SEQUENCE: 28
tcgagggccg taattgtgcg tacacaacag                                    30

<210> SEQ ID NO 29
<211> LENGTH: 30
<212> TYPE: DNA
<213> ORGANISM: Artificial Sequence
<220> FEATURE:
<223> OTHER INFORMATION: 14DR CAST-7

<400> SEQUENCE: 29
tcgagggccg taattgtgcg tacacaacag                                    30

<210> SEQ ID NO 30
<211> LENGTH: 30
<212> TYPE: DNA
<213> ORGANISM: Artificial Sequence
<220> FEATURE:
<223> OTHER INFORMATION: 12DR CAST-8

<400> SEQUENCE: 30
acttgtgaac gctacgctcc acatagtcga                                    30

<210> SEQ ID NO 31
<211> LENGTH: 30
<212> TYPE: DNA
<213> ORGANISM: Artificial Sequence
<220> FEATURE:
<223> OTHER INFORMATION: 14DR CAST-8

<400> SEQUENCE: 31
acttgtgaac gctacgctcc acatagtcga                                    30

```
<210> SEQ ID NO 32
<211> LENGTH: 30
<212> TYPE: DNA
<213> ORGANISM: Artificial Sequence
<220> FEATURE:
<223> OTHER INFORMATION: 12DR CAST-9

<400> SEQUENCE: 32
cccaggtcag agatttaagt acatggtgca                                              30

<210> SEQ ID NO 33
<211> LENGTH: 30
<212> TYPE: DNA
<213> ORGANISM: Artificial Sequence
<220> FEATURE:
<223> OTHER INFORMATION: 14DR CAST-9

<400> SEQUENCE: 33
cccaggtcag agatttaagt acatggtgca                                              30

<210> SEQ ID NO 34
<211> LENGTH: 30
<212> TYPE: DNA
<213> ORGANISM: Artificial Sequence
<220> FEATURE:
<223> OTHER INFORMATION: 12DR CAST-10

<400> SEQUENCE: 34
gacggcgccc gtattttgc atactggggc                                               30

<210> SEQ ID NO 35
<211> LENGTH: 30
<212> TYPE: DNA
<213> ORGANISM: Artificial Sequence
<220> FEATURE:
<223> OTHER INFORMATION: 14DR CAST-10

<400> SEQUENCE: 35
gacggcgccc gtattttgc atactggggc                                               30

<210> SEQ ID NO 36
<211> LENGTH: 30
<212> TYPE: DNA
<213> ORGANISM: Artificial Sequence
<220> FEATURE:
<223> OTHER INFORMATION: 12DR CAST-11

<400> SEQUENCE: 36
ctactgacgc ggagcataat tttgcataca                                              30

<210> SEQ ID NO 37
<211> LENGTH: 31
<212> TYPE: DNA
<213> ORGANISM: Artificial Sequence
<220> FEATURE:
<223> OTHER INFORMATION: 14DR CAST-11

<400> SEQUENCE: 37
ctactggacg cggagcataa ttttgcatac a                                            31

<210> SEQ ID NO 38
<211> LENGTH: 30
<212> TYPE: DNA
<213> ORGANISM: Artificial Sequence
<220> FEATURE:
<223> OTHER INFORMATION: 12DR CAST-12
```

```
<400> SEQUENCE: 38
cgatttagtc gtccgttcat aagtacacgt                                      30

<210> SEQ ID NO 39
<211> LENGTH: 30
<212> TYPE: DNA
<213> ORGANISM: Artificial Sequence
<220> FEATURE:
<223> OTHER INFORMATION: 14DR CAST-12

<400> SEQUENCE: 39
cgatttagtc gtccgttcat aagtacacgt                                      30

<210> SEQ ID NO 40
<211> LENGTH: 30
<212> TYPE: DNA
<213> ORGANISM: Artificial Sequence
<220> FEATURE:
<223> OTHER INFORMATION: 12DR CAST-20

<400> SEQUENCE: 40
gtctttgtgt acacagtatg tacacttacg                                      30

<210> SEQ ID NO 41
<211> LENGTH: 30
<212> TYPE: DNA
<213> ORGANISM: Artificial Sequence
<220> FEATURE:
<223> OTHER INFORMATION: 14DR CAST-20

<400> SEQUENCE: 41
gtctttgtgt acacagtatg tacacttacg                                      30

<210> SEQ ID NO 42
<211> LENGTH: 33
<212> TYPE: DNA
<213> ORGANISM: Artificial Sequence
<220> FEATURE:
<223> OTHER INFORMATION: SB left outer 14 DR

<400> SEQUENCE: 42
tacagttgaa gtcggaagtt tacatacact tag                                  33

<210> SEQ ID NO 43
<211> LENGTH: 32
<212> TYPE: DNA
<213> ORGANISM: Artificial Sequence
<220> FEATURE:
<223> OTHER INFORMATION: SB left inner 12 DR

<400> SEQUENCE: 43
cccagtgggt cagaagttta catacactaa gt                                   32

<210> SEQ ID NO 44
<211> LENGTH: 41
<212> TYPE: DNA
<213> ORGANISM: Artificial Sequence
<220> FEATURE:
<223> OTHER INFORMATION: CAST-2 sense probe

<400> SEQUENCE: 44
acatacaccc tggtgtatgt aaagatcgga cggccggttg g                         41

<210> SEQ ID NO 45
```

```
<211> LENGTH: 45
<212> TYPE: DNA
<213> ORGANISM: Artificial Sequence
<220> FEATURE:
<223> OTHER INFORMATION: CAST-2 AS probe

<400> SEQUENCE: 45
gactccaacc ggccgtccga tctttacata caccagggtg tatgt            45

<210> SEQ ID NO 46
<211> LENGTH: 41
<212> TYPE: DNA
<213> ORGANISM: Artificial Sequence
<220> FEATURE:
<223> OTHER INFORMATION: CAST-5 S probe

<400> SEQUENCE: 46
acatacaggc gcgtgtatgt acacttgggg tcgtcacttg g                41

<210> SEQ ID NO 47
<211> LENGTH: 45
<212> TYPE: DNA
<213> ORGANISM: Artificial Sequence
<220> FEATURE:
<223> OTHER INFORMATION: CAST-5 AS probe

<400> SEQUENCE: 47
gactccaagt gacgacccca agtgtacata cacgcgcctg tatgt            45

<210> SEQ ID NO 48
<211> LENGTH: 41
<212> TYPE: DNA
<213> ORGANISM: Artificial Sequence
<220> FEATURE:
<223> OTHER INFORMATION: CAST-9 S probe

<400> SEQUENCE: 48
acatacagca ccatgtactt aaatctctga cctgggcttg g                41

<210> SEQ ID NO 49
<211> LENGTH: 45
<212> TYPE: DNA
<213> ORGANISM: Artificial Sequence
<220> FEATURE:
<223> OTHER INFORMATION: CAST-9 AS probe

<400> SEQUENCE: 49
gactccaagc ccaggtcaga gatttaagta catggtgctg tatgt            45

<210> SEQ ID NO 50
<211> LENGTH: 41
<212> TYPE: DNA
<213> ORGANISM: Artificial Sequence
<220> FEATURE:
<223> OTHER INFORMATION: CAST-20 S probe

<400> SEQUENCE: 50
acatacacgt aagtgtacat actgtgtaca caaagacttg g                41

<210> SEQ ID NO 51
<211> LENGTH: 45
<212> TYPE: DNA
<213> ORGANISM: Artificial Sequence
<220> FEATURE:
<223> OTHER INFORMATION: CAST-20 AS probe

<400> SEQUENCE: 51
```
gactccaagt ctttgtgtac acagtatgta cacttacgtg tatgt    45

<210> SEQ ID NO 52
<211> LENGTH: 86
<212> TYPE: DNA
<213> ORGANISM: Artificial Sequence
<220> FEATURE:
<223> OTHER INFORMATION: SB-DOL random 35 bp long core
<220> FEATURE:
<221> NAME/KEY: misc_feature
<222> LOCATION: 27..61
<223> OTHER INFORMATION: /allele="random core: C, T, G or A"

<400> SEQUENCE: 52
gcgggatcca ctccaggccg gatgctnnnn nnnnnnnnnn nnnnnnnnnn nnnnnnnnnn    60
ncaccagggt gtaaggcgga tcccgc    86

<210> SEQ ID NO 53
<211> LENGTH: 25
<212> TYPE: DNA
<213> ORGANISM: Artificial Sequence
<220> FEATURE:
<223> OTHER INFORMATION: Primer A

<400> SEQUENCE: 53
gcgggatccg ccttacaccc tggtg    25

<210> SEQ ID NO 54
<211> LENGTH: 26
<212> TYPE: DNA
<213> ORGANISM: Artificial Sequence
<220> FEATURE:
<223> OTHER INFORMATION: Primer B

<400> SEQUENCE: 54
gcgggatcca ctccaggccg gatgct    26

<210> SEQ ID NO 55
<211> LENGTH: 32
<212> TYPE: DNA
<213> ORGANISM: Artificial Sequence
<220> FEATURE:
<223> OTHER INFORMATION: SEQ ID NO:3 of US 8,227,432 outer DR

<400> SEQUENCE: 55
cagttgaagt cggaagttta catacacyta ag    32

<210> SEQ ID NO 56
<211> LENGTH: 32
<212> TYPE: DNA
<213> ORGANISM: Artificial Sequence
<220> FEATURE:
<223> OTHER INFORMATION: SEQ ID NO:4 of US 8,227,432 inner DR

<400> SEQUENCE: 56
yccagtgggt cagaagttta catacactma rt    32

<210> SEQ ID NO 57
<211> LENGTH: 44
<212> TYPE: DNA
<213> ORGANISM: Artificial Sequence
<220> FEATURE:
<223> OTHER INFORMATION: Primer

<400> SEQUENCE: 57
tacagtgacg accccaagtg tacatacacg cgccccaaat acat    44

<210> SEQ ID NO 58
<211> LENGTH: 46
<212> TYPE: DNA
<213> ORGANISM: Artificial Sequence
<220> FEATURE:
<223> OTHER INFORMATION: primer

<400> SEQUENCE: 58
tacagtgacg accccaagtg tacatacacg cgccttggag tcatta    46

<210> SEQ ID NO 59
<211> LENGTH: 39
<212> TYPE: DNA
<213> ORGANISM: Artificial Sequence
<220> FEATURE:
<223> OTHER INFORMATION: primer

<400> SEQUENCE: 59
gtacatacac gcgcttagta tttggtagca ttgcccttta    39

<210> SEQ ID NO 60
<211> LENGTH: 39
<212> TYPE: DNA
<213> ORGANISM: Artificial Sequence
<220> FEATURE:
<223> OTHER INFORMATION: primer

<400> SEQUENCE: 60
gtacatacac gcgcttgact gtgcctttaa acagcttgg    39

<210> SEQ ID NO 61
<211> LENGTH: 42
<212> TYPE: DNA
<213> ORGANISM: Artificial Sequence
<220> FEATURE:
<223> OTHER INFORMATION: primer

<400> SEQUENCE: 61
acttggggtc gtcaccaatt gtgatacagt gaattataag tg    42

<210> SEQ ID NO 62
<211> LENGTH: 40
<212> TYPE: DNA
<213> ORGANISM: Artificial Sequence
<220> FEATURE:
<223> OTHER INFORMATION: primer

<400> SEQUENCE: 62
acttggggtc gtcaccgaat gtgatgaaag aaataaaagc    40

<210> SEQ ID NO 63
<211> LENGTH: 39
<212> TYPE: DNA
<213> ORGANISM: Artificial Sequence
<220> FEATURE:
<223> OTHER INFORMATION: primer

<400> SEQUENCE: 63
gtacatacac gcgcttagta tttggtagca ttgcccttta    39

<210> SEQ ID NO 64
<211> LENGTH: 39
<212> TYPE: DNA
<213> ORGANISM: Artificial Sequence

```
<220> FEATURE:
<223> OTHER INFORMATION: primer

<400> SEQUENCE: 64
gtacatacac gcgcttgact gtgcctttaa acagcttgg                              39

<210> SEQ ID NO 65
<211> LENGTH: 42
<212> TYPE: DNA
<213> ORGANISM: Artificial Sequence
<220> FEATURE:
<223> OTHER INFORMATION: primer

<400> SEQUENCE: 65
acttggggtc gtcaccaatt gtgatacagt gaattataag tg                          42

<210> SEQ ID NO 66
<211> LENGTH: 40
<212> TYPE: DNA
<213> ORGANISM: Artificial Sequence
<220> FEATURE:
<223> OTHER INFORMATION: primer

<400> SEQUENCE: 66
acttggggtc gtcaccgaat gtgatgaaag aaataaaagc                             40

<210> SEQ ID NO 67
<211> LENGTH: 42
<212> TYPE: DNA
<213> ORGANISM: Artificial Sequence
<220> FEATURE:
<223> OTHER INFORMATION: primer

<400> SEQUENCE: 67
acttccgact tcaactgtag gggatcctct agagtcgacc tg                          42

<210> SEQ ID NO 68
<211> LENGTH: 42
<212> TYPE: DNA
<213> ORGANISM: Artificial Sequence
<220> FEATURE:
<223> OTHER INFORMATION: primer

<400> SEQUENCE: 68
acttccgact tcaactgtag ggtaccgagc tcgaattcac tg                          42

<210> SEQ ID NO 69
<211> LENGTH: 41
<212> TYPE: DNA
<213> ORGANISM: Artificial Sequence
<220> FEATURE:
<223> OTHER INFORMATION: primer

<400> SEQUENCE: 69
gtacatacac gcgccccaaa tacatttaaa ctcactttt c                            41

<210> SEQ ID NO 70
<211> LENGTH: 40
<212> TYPE: DNA
<213> ORGANISM: Artificial Sequence
<220> FEATURE:
<223> OTHER INFORMATION: primer

<400> SEQUENCE: 70
gtacatacac gcgccttgga gtcattaaaa ctcgttttc                              40
```

<210> SEQ ID NO 71
<211> LENGTH: 40
<212> TYPE: DNA
<213> ORGANISM: Artificial Sequence
<220> FEATURE:
<223> OTHER INFORMATION: primer

<400> SEQUENCE: 71
acttctgacc cactgggaat gtgatgaaag aaataaaagc                40

<210> SEQ ID NO 72
<211> LENGTH: 42
<212> TYPE: DNA
<213> ORGANISM: Artificial Sequence
<220> FEATURE:
<223> OTHER INFORMATION: primer

<400> SEQUENCE: 72
acttctgacc cactggaatt gtgatacagt gaattataag tg             42

<210> SEQ ID NO 73
<211> LENGTH: 39
<212> TYPE: DNA
<213> ORGANISM: Artificial Sequence
<220> FEATURE:
<223> OTHER INFORMATION: primer

<400> SEQUENCE: 73
gtacatacac gcgcttagta tttggtagca ttgccttta                 39

<210> SEQ ID NO 74
<211> LENGTH: 39
<212> TYPE: DNA
<213> ORGANISM: Artificial Sequence
<220> FEATURE:
<223> OTHER INFORMATION: primer

<400> SEQUENCE: 74
gtacatacac gcgcttgact gtgccttaa acagcttgg                  39

<210> SEQ ID NO 75
<211> LENGTH: 39
<212> TYPE: DNA
<213> ORGANISM: Artificial Sequence
<220> FEATURE:
<223> OTHER INFORMATION: primer

<400> SEQUENCE: 75
gtacatacac gcgcttagta tttggtagca ttgccttta                 39

<210> SEQ ID NO 76
<211> LENGTH: 39
<212> TYPE: DNA
<213> ORGANISM: Artificial Sequence
<220> FEATURE:
<223> OTHER INFORMATION: primer

<400> SEQUENCE: 76
gtacatacac gcgcttgact gtgccttaa acagcttgg                  39

<210> SEQ ID NO 77
<211> LENGTH: 40
<212> TYPE: DNA
<213> ORGANISM: Artificial Sequence
<220> FEATURE:
<223> OTHER INFORMATION: primer

```
<400> SEQUENCE: 77
acttctgacc cactgggaat gtgatgaaag aaataaaagc                           40

<210> SEQ ID NO 78
<211> LENGTH: 42
<212> TYPE: DNA
<213> ORGANISM: Artificial Sequence
<220> FEATURE:
<223> OTHER INFORMATION: primer

<400> SEQUENCE: 78
acttctgacc cactggaatt gtgatacagt gaattataag tg                       42

<210> SEQ ID NO 79
<211> LENGTH: 41
<212> TYPE: DNA
<213> ORGANISM: Artificial Sequence
<220> FEATURE:
<223> OTHER INFORMATION: 14 DR probe S

<400> SEQUENCE: 79
acatacactt aagtgtatgt aaacttccga cttcaacttg g                        41

<210> SEQ ID NO 80
<211> LENGTH: 45
<212> TYPE: DNA
<213> ORGANISM: Artificial Sequence
<220> FEATURE:
<223> OTHER INFORMATION: 14 DR probe AS

<400> SEQUENCE: 80
gactccaagt tgaagtcgga agtttacata cacttaagtg tatgt                    45

<210> SEQ ID NO 81
<211> LENGTH: 39
<212> TYPE: DNA
<213> ORGANISM: Artificial Sequence
<220> FEATURE:
<223> OTHER INFORMATION: 12 DR probe S

<400> SEQUENCE: 81
acatacatta gtgtatgtaa acttctgacc cactgttgg                           39

<210> SEQ ID NO 82
<211> LENGTH: 43
<212> TYPE: DNA
<213> ORGANISM: Artificial Sequence
<220> FEATURE:
<223> OTHER INFORMATION: 12 DR probe AS

<400> SEQUENCE: 82
gactccaaca gtgggtcaga agtttacata cactaatgta tgt                      43

<210> SEQ ID NO 83
<211> LENGTH: 21
<212> TYPE: RNA
<213> ORGANISM: Artificial Sequence
<220> FEATURE:
<223> OTHER INFORMATION: scramble - as

<400> SEQUENCE: 83
taggtcctct tcatcttgtt g                                              21

<210> SEQ ID NO 84
```

```
<211> LENGTH: 21
<212> TYPE: RNA
<213> ORGANISM: Artificial Sequence
<220> FEATURE:
<223> OTHER INFORMATION: scramble -ss

<400> SEQUENCE: 84
caacaagatg aagagcacct a                                              21

<210> SEQ ID NO 85
<211> LENGTH: 21
<212> TYPE: RNA
<213> ORGANISM: Artificial Sequence
<220> FEATURE:
<223> OTHER INFORMATION: ssrp1 - as

<400> SEQUENCE: 85
tttaccagtg ctttcatgag g                                              21

<210> SEQ ID NO 86
<211> LENGTH: 21
<212> TYPE: RNA
<213> ORGANISM: Artificial Sequence
<220> FEATURE:
<223> OTHER INFORMATION: ssrp1 - ss

<400> SEQUENCE: 86
ggtcatgaaa gcactggtaa a                                              21

<210> SEQ ID NO 87
<211> LENGTH: 21
<212> TYPE: RNA
<213> ORGANISM: Artificial Sequence
<220> FEATURE:
<223> OTHER INFORMATION: supt16H - as

<400> SEQUENCE: 87
atcaaagtgc gaacaaggtt g                                              21

<210> SEQ ID NO 88
<211> LENGTH: 21
<212> TYPE: RNA
<213> ORGANISM: Artificial Sequence
<220> FEATURE:
<223> OTHER INFORMATION: supt16H - ss

<400> SEQUENCE: 88
caaccttgtt cgcactttga t                                              21

<210> SEQ ID NO 89
<211> LENGTH: 23
<212> TYPE: DNA
<213> ORGANISM: Artificial Sequence
<220> FEATURE:
<223> OTHER INFORMATION: Supt16H - Forward primer

<400> SEQUENCE: 89
cattggtgac acagtgcttg tgg                                            23

<210> SEQ ID NO 90
<211> LENGTH: 22
<212> TYPE: DNA
<213> ORGANISM: Artificial Sequence
<220> FEATURE:
<223> OTHER INFORMATION: Supt16H - Reverse primer

<400> SEQUENCE: 90
```

```
ccaaaaggtc ctctgcctca tc                                        22

<210> SEQ ID NO 91
<211> LENGTH: 22
<212> TYPE: DNA
<213> ORGANISM: Artificial Sequence
<220> FEATURE:
<223> OTHER INFORMATION: Ssrp1 - Forward primer

<400> SEQUENCE: 91
tcacagtgcc aggcaacttc ca                                        22

<210> SEQ ID NO 92
<211> LENGTH: 22
<212> TYPE: DNA
<213> ORGANISM: Artificial Sequence
<220> FEATURE:
<223> OTHER INFORMATION: Ssrp1 - Reverse primer

<400> SEQUENCE: 92
acaggtggct tgtggacgta ga                                        22
```